United States Patent
Jethrow et al.

(10) Patent No.: US 7,871,565 B2
(45) Date of Patent: Jan. 18, 2011

(54) METHOD FOR GENERATING A MICROBIAL DEACTIVATION FLUID IN AN APPARATUS FOR DEACTIVATING INSTRUMENTS AND DEVICES

(75) Inventors: Christopher A. Jethrow, Maple Heights, OH (US); John J. Mayer, Painesville, OH (US); Dana M. Hall, Mentor, OH (US); Donald G. Rosenhamer, Garfield Heights, OH (US)

(73) Assignee: American Sterilizer Company, Mentor, OH (US)

( * ) Notice: Subject to any disclaimer, the term of this patent is extended or adjusted under 35 U.S.C. 154(b) by 988 days.

(21) Appl. No.: 11/714,035

(22) Filed: Mar. 5, 2007

(65) Prior Publication Data

US 2007/0212252 A1 Sep. 13, 2007

(51) Int. Cl.
 A61L 2/18 (2006.01)
(52) U.S. Cl. .............................. 422/28; 422/29; 422/31
(58) Field of Classification Search ................... 422/28, 422/31, 34, 29
 See application file for complete search history.

(56) References Cited

U.S. PATENT DOCUMENTS

| | | | |
|---|---|---|---|
| 2,006,085 A | 6/1935 | Lehmkuhl | 422/275 |
| 4,491,414 A | 1/1985 | Hayatdavoudi et al. | 366/6 |
| 4,771,945 A | 9/1988 | Martin | 239/13 |
| 4,865,061 A | 9/1989 | Fowler et al. | 134/108 |
| 4,909,999 A | 3/1990 | Cummings et al. | 422/298 |
| 4,941,519 A | 7/1990 | Sestak et al. | 141/22 |
| 5,116,575 A * | 5/1992 | Badertscher et al. | 422/28 |
| 5,209,909 A | 5/1993 | Siegel et al. | 422/292 |
| 5,494,644 A | 2/1996 | Thomas et al. | 422/261 |
| 5,595,711 A | 1/1997 | Wilson et al. | 422/119 |
| 5,662,866 A | 9/1997 | Siegel et al. | 422/29 |
| 5,759,501 A | 6/1998 | Livingston et al. | 422/275 |
| 5,858,305 A | 1/1999 | Malchesky | 422/28 |
| 5,863,499 A | 1/1999 | Kralovic | 422/32 |
| 5,932,171 A | 8/1999 | Malchesky | 422/29 |
| 5,997,814 A | 12/1999 | Minerovic et al. | 422/29 |
| 6,158,580 A | 12/2000 | Davis | 206/204 |
| 6,197,814 B1 | 3/2001 | Arata | 514/495 |
| 6,325,968 B1 | 12/2001 | Fricker et al. | 422/28 |
| 6,482,358 B1 | 11/2002 | Kelsch et al. | 422/28 |

(Continued)

FOREIGN PATENT DOCUMENTS

WO WO 95/02330 * 1/1995

(Continued)

*Primary Examiner*—Sean E Conley
(74) *Attorney, Agent, or Firm*—Kusner & Jaffe; Michael A. Centanni

(57) ABSTRACT

A method of generating a microbial deactivation fluid to circulate through an apparatus that has a decontamination chamber for holding medical instruments and devices, comprising the steps of:
 (a) providing a first compartment and a second compartment in the circulation system;
 (b) providing a chemical reagent in the first compartment and a builder composition in the second compartment;
 (c) causing a fluid to flow through the second compartment to mix with the builder composition to create an alkaline fluid;
 (d) when the alkaline fluid has reached a predetermined pH level, causing the alkaline fluid to flow through the first compartment to mix with the chemical reagent to dissolve the chemical reagent to generate a microbial deactivation fluid; and
 (e) continuing steps (c) and (d) to continue the generation of the microbial deactivation fluid.

29 Claims, 30 Drawing Sheets

U.S. PATENT DOCUMENTS

| | | | |
|---|---|---|---|
| 6,582,654 B1 | 6/2003 | Kral et al. | 422/28 |
| 6,749,807 B1 * | 6/2004 | Schindly et al. | 422/28 |
| 6,942,224 B2 | 9/2005 | Ludwig et al. | 277/637 |
| 6,979,428 B2 | 12/2005 | Jethrow et al. | 422/292 |
| 7,135,142 B2 | 11/2006 | Burke et al. | 422/28 |
| 2003/0070696 A1 | 4/2003 | Fricker et al. | 134/42 |
| 2004/0178153 A1 | 9/2004 | Morse et al. | 210/788 |
| 2005/0025664 A1 | 2/2005 | Selig et al. | 422/28 |
| 2005/0025671 A1 | 2/2005 | Kral et al. | 422/62 |
| 2005/0025683 A1 | 2/2005 | Horacek et al. | 422/275 |
| 2005/0025685 A1 | 2/2005 | Selig et al. | 422/292 |
| 2005/0025686 A1 | 2/2005 | Sargent et al. | 422/300 |
| 2006/0127289 A1 | 6/2006 | Selig et al. | 422/300 |
| 2007/0207074 A1 | 9/2007 | Jethrow | 422/292 |
| 2007/0212278 A1 | 9/2007 | Jethrow et al. | 422/292 |
| 2007/0212279 A1 | 9/2007 | Mayer et al. | 422/292 |
| 2007/0212280 A1 | 9/2007 | Horacek et al. | 422/292 |
| 2007/0212283 A1 | 9/2007 | Horacek et al. | 422/300 |
| 2007/0212284 A1 | 9/2007 | Solomon et al. | 422/307 |

FOREIGN PATENT DOCUMENTS

| | | |
|---|---|---|
| WO | WO 00/69475 | 11/2000 |

* cited by examiner

METHOD FOR GENERATING A MICROBIAL DEACTIVATION FLUID IN AN APPARATUS FOR DEACTIVATING INSTRUMENTS AND DEVICES

FIELD OF THE INVENTION

The present invention relates to disinfection or deactivation of medical, dental, pharmaceutical, veterinary or mortuary instruments and devices, and more particularly, to a method and apparatus for deactivating items and for maintaining such items in a deactivated state.

BACKGROUND OF THE INVENTION

Medical, dental, pharmaceutical, veterinary or mortuary instruments and devices are routinely exposed to blood or other body fluids during medical procedures. Following such procedures, a thorough cleaning and anti-microbial deactivation of the instruments is required before subsequent use. Liquid microbial deactivation systems are now widely used to clean and deactivate instruments and devices that cannot withstand the high temperature of a steam deactivation system. Liquid microbial deactivation systems typically operate by exposing the medical devices and/or instruments to a liquid disinfectant or a deactivation composition, such as peracetic acid or some other strong oxidant. In such systems, the instruments or devices to be cleaned are typically placed within a deactivation chamber within the deactivation system, or in a container that is placed within the deactivation chamber. During a deactivation cycle, a liquid disinfectant is then circulated through the deactivation chamber (and the container therein).

The present invention provides a method and apparatus for microbially deactivating medical instruments and devices.

SUMMARY OF THE INVENTION

In accordance with the present invention, there is provided in an apparatus for deactivating medical instruments and devices having a circulation system for circulating a fluid through a decontamination chamber for holding medical instruments and devices, a method of generating a microbial deactivation fluid and exposing the devices to the microbial deactivation fluid comprising the steps of:

(a) providing a first compartment and a second compartment in the circulation system;

(b) providing a chemical reagent in a first compartment and a builder composition in a second compartment;

(c) causing a fluid to flow through the second compartment to mix with the builder composition to create an alkaline fluid;

(d) when the alkaline fluid has reached a predetermined pH level, causing the alkaline fluid to flow through the first compartment to mix with the chemical reagent to dissolve the chemical reagent to generate a microbial deactivation fluid;

(e) continuing steps (c) and (d) to continue the generation of the microbial deactivation fluid; and (f) when the microbial deactivation fluid has reached a minimum predetermined concentration, causing the microbial deactivation fluid to flow through the decontamination chamber.

In accordance with another aspect of the present invention, there is provided in an apparatus for deactivating medical instruments and devices having a circulation system for circulating a fluid through a decontamination chamber for holding medical instruments and devices, a method of generating a microbial deactivation fluid comprising the steps of:

(a) providing a first compartment and a second compartment in the circulation system;

(b) providing a chemical reagent in a first compartment and a builder composition in a second compartment;

(c) causing a fluid having a temperature between about 45° C. and about 60° C. to flow through the second compartment to mix with the builder composition to create an alkaline fluid;

(d) when the alkaline fluid has reached a predetermined pH level, causing the alkaline fluid to flow through the first compartment to mix with the chemical reagent to dissolve the chemical reagent to generate a microbial deactivation; and (e) continuing steps (c) and (d) to continue the generation of the microbial deactivation fluid.

In accordance with yet another aspect of the present invention, there is provided in an apparatus for deactivating medical instruments and devices having a circulation system for circulating a fluid through a decontamination chamber for holding medical instruments and devices, a method of generating a microbial deactivation fluid comprising the steps of:

(a) providing a first compartment and a second compartment in the circulation system;

(b) providing a chemical reagent in the first compartment and a builder composition in the second compartment;

(c) causing a fluid to flow through the second compartment to mix with the builder composition to create an alkaline fluid;

(d) when the alkaline fluid has reached a predetermined pH level, causing the alkaline fluid to flow through the first compartment to mix with the chemical reagent to dissolve the chemical reagent to generate a microbial deactivation fluid; and (e) continuing steps (c) and (d) to continue the generation of the microbial deactivation fluid.

In accordance with still another aspect of the present invention, there is provided in an apparatus for deactivating medical instruments and devices having a circulation system for circulating a fluid through a decontamination chamber for holding medical instruments and devices, a method of generating a microbial deactivation fluid comprising the steps of:

(a) providing a first compartment and a second compartment in the circulation system;

(b) providing a chemical reagent in the first compartment and a builder composition in the second compartment;

(c) causing a fluid to flow through the second compartment to mix with the builder composition to create an alkaline fluid;

(d) after a predetermined amount of time, causing the alkaline solution to flow through the first compartment to mix with the chemical reagent to dissolve the chemical reagent to generate a microbial deactivation fluid; and (e) continuing steps (c) and (d) to continue the generation of the microbial deactivation fluid.

One advantage of the present invention is an apparatus for deactivating medical instruments and items.

Another advantage of the present invention is a container for holding medical instruments and items during a microbial deactivation process, which container maintains the instruments in a deactivated environment therein for a prolonged period of time after removal of the container from the apparatus.

A still further advantage of the present invention is a container as described above that may be used as a storage device for storing the microbially deactivated instruments.

Another advantage of the present invention is a compact, front-loading apparatus for deactivating medical instruments and items.

A still further advantage of the present invention is an apparatus as described above having a drawer system that opens at a downward angle to a user.

Another advantage of the present invention is an apparatus for deactivating medical instruments and items having a circulation system that allows for separate rinsing of a chemistry container that is used to generate a microbial deactivation fluid.

A still further advantage of the present invention is an apparatus for deactivating medical instruments and items having a chemistry container that can be easily modified to accommodate different chemistries.

A still further advantage of the present invention is an apparatus for deactivating medical instruments and items that utilizes an instrument container that can be configured to include different instruments and devices.

Another advantage of the present invention is an apparatus for deactivating medical instruments and items that circulates a deactivation fluid through sterile water filters to prevent the growth of microorganisms on filter membrane.

Another advantage of the present invention is an apparatus for deactivating medical instruments and items that utilizes a two-part dry chemistry.

A still further advantage of the present invention is an apparatus for deactivating medical instruments and items that utilizes a chemistry container that has a connector-less design.

A still further advantage of the present invention is an apparatus for deactivating medical instruments and items having a high-pressure zone and a low-pressure zone to induce constant flow of deactivation fluid through the apparatus.

A still further advantage of the present invention is a method for quickly generating a microbial deactivation fluid from dry chemistry.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
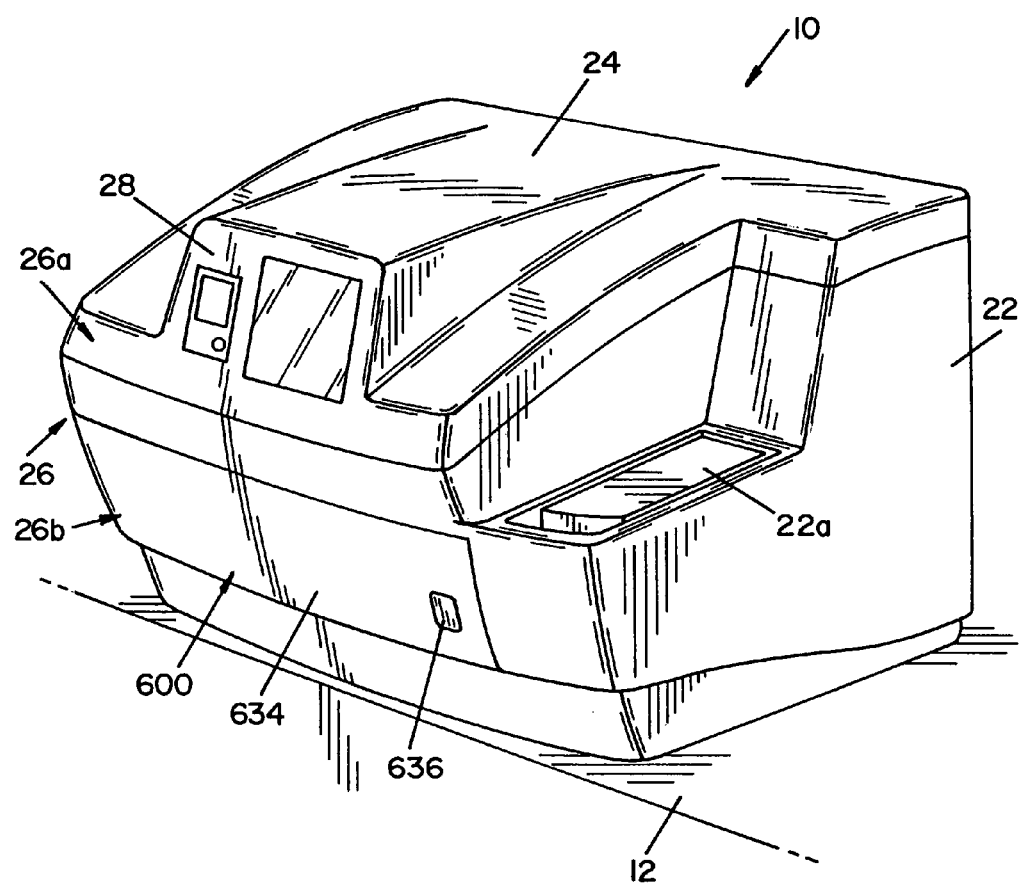
FIG. 1 is a perspective view of an automated reprocessor for microbially deactivating medical instruments, according to the present invention.

Referring now to the drawings wherein the showings are for the purpose of illustrating a preferred embodiment of the invention only, and not for the purpose of limiting same, FIG.

1 shows an apparatus 10 for microbially deactivating medical instruments and other devices, illustrating a preferred embodiment of the present invention. Apparatus 10 is designed to rest upon a table or countertop 12, as illustrated in FIG. 1. Countertop 12 in and of itself forms no part of the present invention. Apparatus 10 includes a housing structure 22 containing the operative components of apparatus 10. Housing structure 22 has an upper surface 24 that slopes generally downward toward a front face 26. Front face 26 has an upper section 26a and a lower section 26b. Upper section 26a includes a display panel 28. Display panel 28 is connected to a controller system (not shown) that controls the operation of apparatus 10.

Figure 2:
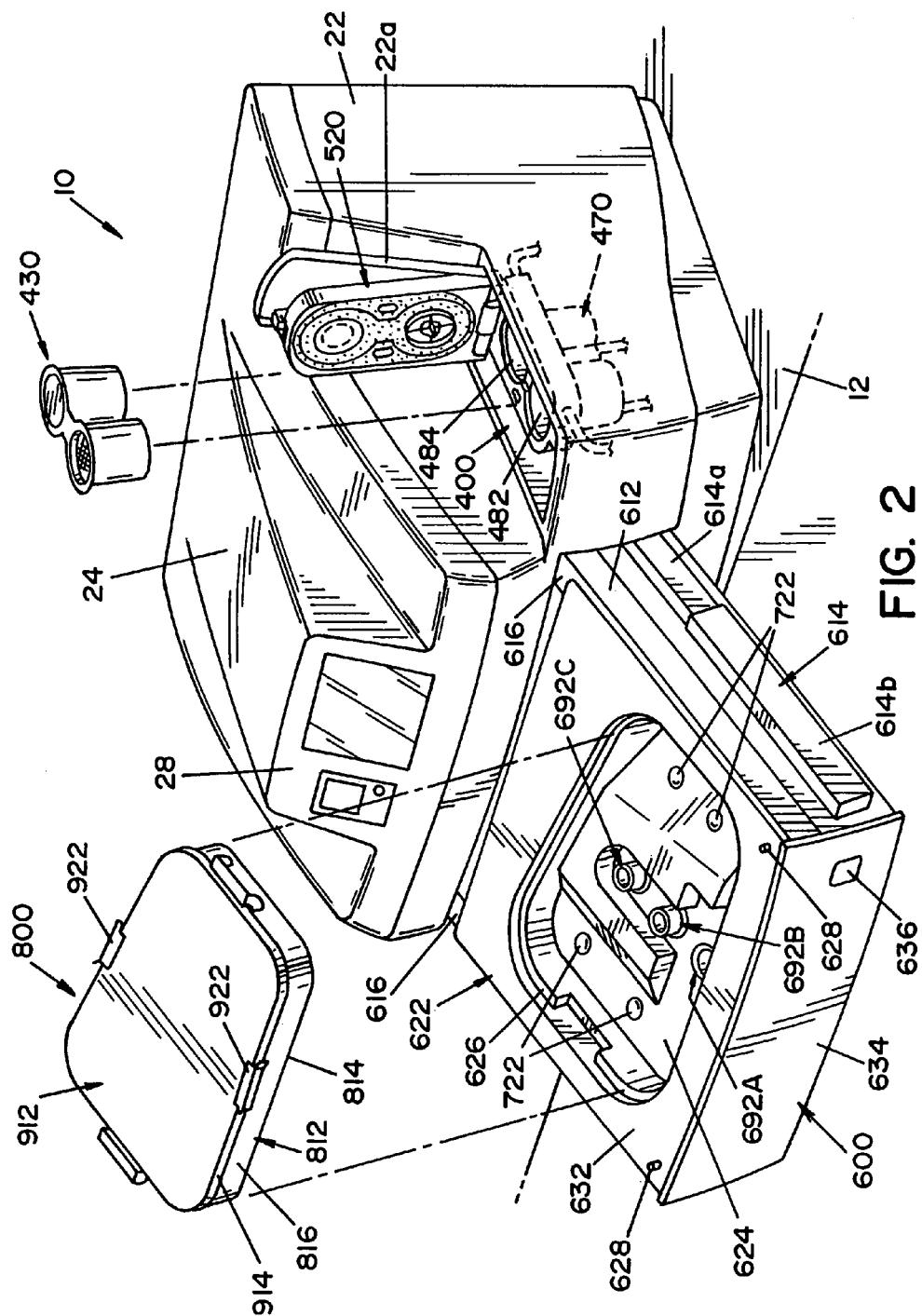
FIG. 2 is a perspective view of the reprocessor of FIG. 1, showing a movable drawer in an opened position and an instrument container removed therefrom, and also showing an access panel to a chemistry delivery system in an opened position and a chemistry container remover therefrom.

A drawer assembly 600 has a front face panel 634 that is coplanar with lower section 26b of front face 26 when drawer assembly 600 is in a closed position, as illustrated in FIG. 1. A drawer actuation button 636 is provided on front panel 634 of drawer assembly 600. Drawer assembly 600 is movable from a closed position, as shown in FIG. 1, to an opened position, as illustrated in FIG. 2. Drawer assembly 600 includes a drawer tray 622 having a flat upper surface 632. A recess or cavity 624 is formed in tray 622, as illustrated in FIG. 2. Surface 632 extends around the periphery of recess or cavity 624. Cavity 624 is dimensioned to receive an instrument container 800. Container 800 is provided to receive the instruments or devices to be deactivated. Container 800 is dimensioned to be received within cavity 624, as illustrated in FIG. 2.

Figure 3:
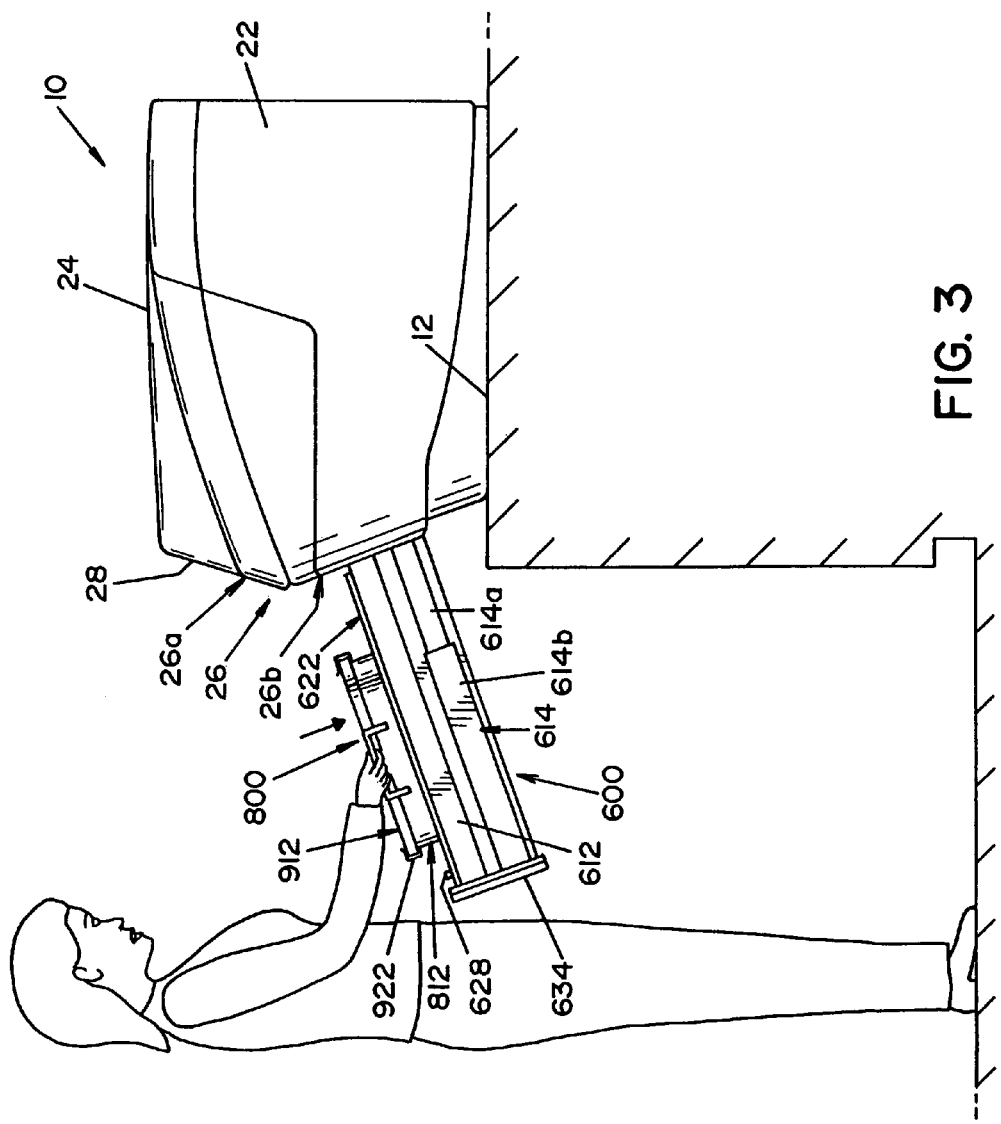
FIG. 3 is a side, elevational view of the reprocessor of FIG. 1, showing the reprocessor on a counter top relative to a user.

A small, rectangular access panel 22a is formed in housing structure 22. In the embodiment shown, access panel 22a is formed to the right side of display panel 28 in a recess formed in housing structure 22. Access panel 22a is movable between a closed position, shown in FIG. 1, and an opened position, shown in FIG. 2. In its opened position, access panel 22a allows access to a chemistry-delivery system 400 that shall be described in greater detail below. Chemistry-delivery system 400 is dimensioned to receive a chemistry-holding device 430 that contains dry chemicals that, when combined with water, form a microbial deactivation fluid used in apparatus 10. As best illustrated in FIG. 3, drawer assembly 600 opens in a generally downward direction. In other words, drawer assembly 600 slides into and out of housing structure 22 in a plane that is sloping downwardly relative to the housing structure 22.

Figure 4:
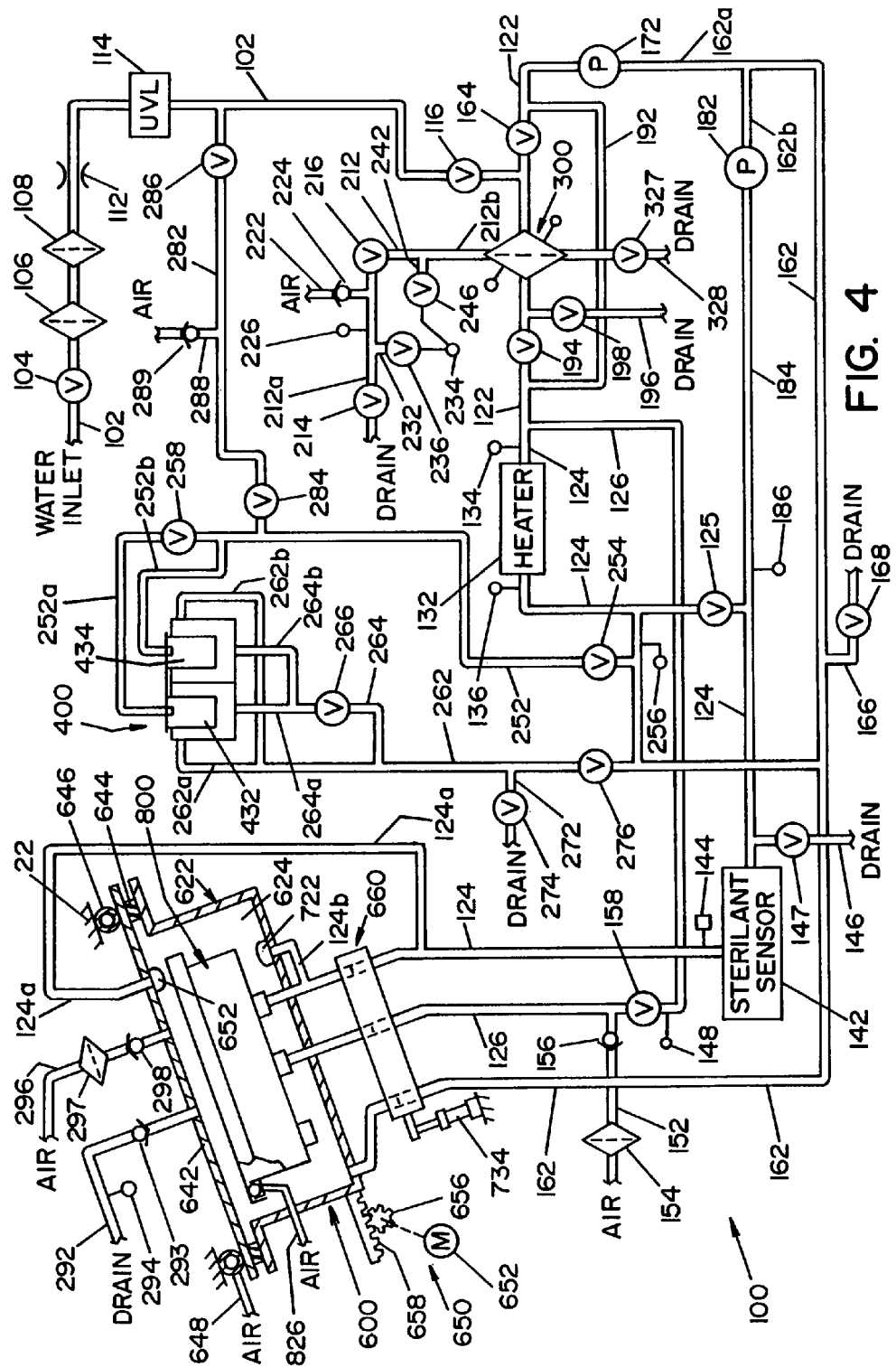
FIG. 4 is a schematic diagram of the reprocessor shown in FIG. 1.
Figure 5:
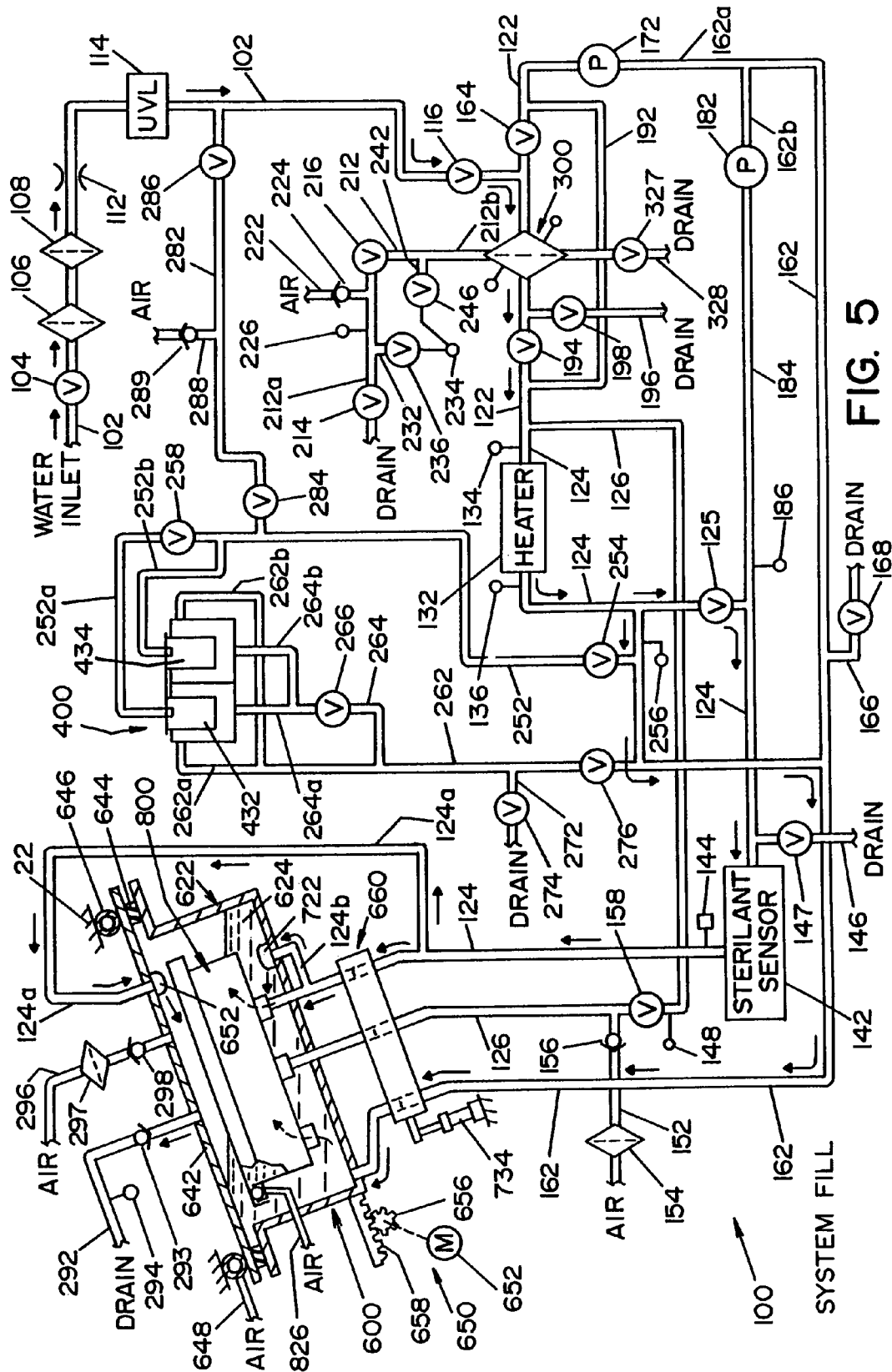
FIG. 5 is a schematic diagram of the reprocessor, illustrating the path of fluids through the reprocessor during a reprocessor fill phase.

Referring now to FIG. 4, a simplified, schematic piping diagram of apparatus 10 is shown. As schematically illustrated in FIG. 3, drawer assembly 600 includes a drive assembly 650, including a rack 658 and a pinion gear 656. Rack 658 is connected to drawer assembly 600 and is movable by pinion gear 656 that is driven by a motor 652. In FIG. 4, instrument container 800 is shown disposed within cavity 624 defined by drawer tray 622. When drawer assembly 600 is in the closed position, as shown in FIG. 4, drawer tray 622 is disposed beneath a plate 642. A static seal element 644 is disposed on the bottom side of plate 642 for contact with the planar portion of drawer tray 622. In this respect, static seal 644 is generally continuous about the periphery of cavity 624 in drawer tray 622. An air-inflatable bladder 646 is provided on the top side of plate 642 to force plate 642 and static seal 644 into sealing engagement with the planar portion of drawer tray 622. Inflatable bladder 646 is disposed between the upper surface of plate 642 and housing structure 22 to force plate 642 into sealing engagement with drawer tray 622. A plurality of springs 647 (best shown in FIG. 18) are connected at one end to the upper side of plate 642 and at the other end to housing structure 22. Springs 647 are tension springs that bias plate 642 and static seal 644 away from the planar portion of drawer tray 622.

As schematically illustrated in FIG. 4, when instrument container 800 is disposed within the recess 624 in drawer tray 622, instrument container 800 is connected to fluid inlet lines and a drain line of a fluid circulation system 100. Instrument container 800 is also in communication with an air conduit 826 for inflating a seal 824 disposed between a tray 812 and a lid 912 of instrument container 800, as shall be described in greater detail below. When drawer assembly 600 is in a closed position and inflatable bladder 646 is activated to force static seal 644 into contact with the planar portion of drawer tray 622, a decontamination chamber is formed within apparatus 10, as schematically illustrated in FIG. 4. Fluid circulation system 100 provides microbial deactivation fluid to the deactivation chamber and is further operable to circulate the microbial deactivation fluid through the decontamination chamber, through instrument container 800 and through instruments contained within instrument container 800.

To enable drawer assembly 600 and drawer tray 622 to move into and out of housing structure 22 of apparatus 10, the input lines and the drain lines from fluid circulation system 100 are attachable and detachable from drawer tray 622 by means of a connector assembly 660 that shall be described in greater detail below.

Fluid circulation system 100 includes a water inlet line 102 that is connected to a source of heated water (not shown). A valve 104 is disposed within water inlet line 102 to control the flow of water into apparatus 10. A pair of macro filters 106, 108 are provided in water inlet line 102 downstream from valve 104 to filter large contaminants that may exist in the incoming water. A flow restrictor 112 is disposed in water inlet line 102 to regulate the flow of water therethrough. An ultraviolet (UV) treatment device 114 for deactivating organisms within the water source is preferably provided in water inlet line 102. A water valve 116 controls the flow of water from water inlet line 102 to a system feeder line 122. System feeder line 122 includes a filter element 300 to filter microscopic organisms from the incoming water source to provide sterile water to fluid circulation system 100.

System feeder line 122 splits into a first branch feeder line 124 and a second branch feeder line 126 downstream of filter element 300. First branch feeder line 124 extends from system feeder line 122, as schematically illustrated in FIG. 4. A heater element 132 is disposed within first branch feeder line 124. A first temperature sensor 134 is disposed within first branch feeder line 124 upstream of heater element 132. First temperature sensor 134 is operable to provide signals to the system controller indicative of the temperature of the water upstream of heater element 132. A second temperature sensor 136 is attached to first branch feeder line 124 downstream of heater element 132 to provide temperature measurements of water downstream of heater element 132. Second temperature sensor 136 is operable to provide signals to the system controller indicative of the temperature of the water downstream of heater element 132. A sterilant sensor 142 is disposed within first branch feeder line 124. Sterilant sensor 142 is operable to provide signals to the system controller indicative of the concentration of a sterilant flowing within first branch feeder line 124. A conductivity probe 144 is attached to first branch feeder line 124 downstream of sterilant sensor 142. Conductivity probe 144 is operable to provide signals to the system controller indicative of the conductivity of the water in first branch feeder line 124. First branch feeder line 124 includes a branch section 124a that extends through the plate in the drawer assembly to communicate with the recess or cavity defined by the drawer tray. A drain line 146 is also connected to first branch feeder line 124 upstream of sterilant sensor 142. A valve 147 is disposed within drain line 146 to control the flow of fluid through drain line 146.

Second branch feeder line 126 also connects to the connector assembly 660. A pressure sensor 148 is disposed within second branch feeder line 126. Pressure sensor 148 is capable of measuring the pressure of the fluid in second branch feeder line 126 and providing a signal that is proportional to the measured pressure to the system controller. An air line 152 is connected to second branch feeder line 126, as illustrated in FIG. 4. Air line 152 is connected to a source (not shown) of dry air. A filter 154 is disposed within air line 152. A directional valve 156 is disposed within air line 152. Directional valve 156 is arranged to allow air to be forced into second branch feeder line 126, but to prevent water or fluids within second branch feeder line 126 from flowing toward the source of air. A valve 158 is disposed within second branch feeder line 126, between pressure sensor 148 and where air line 152 connects to second branch feeder line 126.

A return line 162 is connected at one end to the connector assembly 660. The other end of return line 162 has a first branch 162a that connects to the inlet side of a pump 172. Pump 172 is preferably a high pressure, low volume pump, as shall be described in greater detail below. Pump 172 preferably is a positive displacement pump that is capable of pumping between about 2 gallons per minute and about 6 gallons per minute. In one embodiment, pump 172 is capable of pumping between about 4 gallons per minute and about 5 gallons per minute. In another embodiment pump 172 is capable of pumping about 3.5 gallons per minute. Pump 172 is capable of pumping between about 20 psig and about 60 psig of fluid pressure. In one embodiment, pump 172 is capable of pumping between about 30 psig and about 50 psig of fluid pressure. In another embodiment, pump 172 is capable of pumping about 40 psig of fluid pressure. The outlet side of pump 172 defines the beginning of system feeder line 122. A valve 164 is disposed within system feeder line 122 between pump 172 and the location where water inlet line 102 joins to system feeder line 122. A drain line 166 is connected to return line 162. A valve 168 is disposed within drain line 166 to control the flow of fluid therethrough.

Return line 162 includes a second branch 162b that connects to the inlet side of a pump 182. Pump 182 is a high volume pump. Pump 182 preferably is a centrifugal pump that is capable of pumping between about 7 gallons per minute and about 15 gallons per minute at between about 5 psig and about 14 psig of fluid pressure. In one embodiment, pump 182 pumps between about 8 gallons per minute and about 12 gallons per minute at between about 7 psig and about 12 psig of fluid pressure. In another embodiment, pump 182 pumps about 10 gallons per minute at about 9 psig of fluid pressure.

Pump 172 pumps between about 10% and about 46% of the total fluid flow in the system and pump 182 pumps between about 54% and about 90% of the total fluid flow in the system. In one embodiment, pump 172 pumps between about 20% and about 35% of the total fluid flow in the system and pump 182 pumps between about 65% and about 80% of the total fluid flow in the system. In another embodiment, pump 172 pumps about 25% of the total fluid flow in the system and pump 182 pumps about 75% of the total fluid flow in the system. The outlet side of pump 182 is connected to an auxiliary system feeder line 184 that is connected to first branch feeder line 124. A pressure sensor 186 is disposed within auxiliary system feeder line 184 at a location preceding the juncture where auxiliary system feeder line 184 connects with first branch feeder line 124. Pressure sensor 186 is capable of measuring the pressure of the fluid in auxiliary system feeder line 184 and providing a signal that is proportional to the measured pressure to the system controller. A valve 125 is disposed in first branch feeder line 124 to control fluid flow in branch feeder line 124. Valve 125 is disposed at a location upstream of the juncture where auxiliary system feeder line 184 connects with first branch feeder line 125. When valve 125 is in a first position, between about 75% and about 100% of the flow in branch feeder line 124 is cable of flowing into auxiliary feeder line 184. In one embodiment, between about 90% to about 100% of the flow in branch feeder line 124 is cable of flowing into auxiliary feeder line 184. In another embodiment, about 100% of the flow in branch feeder line 124 is cable of flowing into auxiliary feeder line 184. When valve 125 is in a second position between about 5% to about 25% of the flow in branch feeder line 124 is cable of flowing into auxiliary feeder line 184. In one embodiment, between about 5% and about 10% of the flow in branch feeder line 124 is cable of flowing into auxiliary feeder line 184. In another embodiment, about 5% of the flow in branch feeder line 124 is cable of flowing into auxiliary feeder line 184.

A filter bypass line 192 communicates with system feeder line 122 on opposite sides of filter element 300. Specifically, one end of bypass line 192 is connected to system feeder line 122 between pump 172 and valve 164. The other end of bypass line 192 communicates with system feeder line 122 downstream of filter element 300, but before the juncture where system feeder line 122 splits into first branch feeder line 124 and second branch feeder line 126. As shown in FIG. 4, a valve 194 is disposed between filter element 300 and downstream of the connection of bypass line 192 to system feeder line 122. A drain line 196 is connected to system feeder line 122 between valve 194 and filter element 300. A valve 198 is disposed within drain line 196 to regulate flow therethrough. A drain line 328 is also connected to filter element 300. A valve 327 is disposed within drain line 328 to control the flow of fluid therethrough. A temperature sensor 332 is connected to filter element 300. Temperature sensor 332 is capable of measuring the temperature of the fluid in filter element 300 and providing a signal that is proportional to the measured temperature to the system controller. A pressure sensor 334 is also connected to filter element 300. Pressure sensor 334 is capable of measuring the pressure of the fluid in filter element 300 and providing a signal that is proportional to the measured pressure to the system controller.

A test line 212 is connected to filter element 300 to conduct integrity tests of filter element 300. As illustrated in FIG. 4, one end of test line 212 is connected to filter element 300 and the other end is connected to a drain. Two spaced-apart valves 214, 216 are disposed in test line 212. Between valves 214 and 216, a first test line section 212a is defined. Between valve 216 and filter element 300, a second test line section 212b is defined. An air line 222 from a source of pressurized, filtered, clean air is connected to test line 212. Air line 222 is connected to test line section 212a between valves 214, 216. A check valve 224 is disposed in air line 222. Check valve 224 is arranged to allow one-way flow of air to test line section 212a. A pressure sensor 226 is disposed in test line section 212a between valves 214, 216 to measure the air pressure in test line section 212a and provide a signal that is proportional to the measured air pressure in test line to the system controller. First test line section 212a includes a T-fitting 232 for connecting first test line section 212a to one side of a differential pressure sensor 234. A valve 236 is disposed in T-fitting 232 to control connection of first test line section 212a to differential pressure sensor 234. A second T-fitting 242 is disposed in second test line section 212b and is connected to a second side of differential pressure sensor 234. Differential pressure sensor 234 is cable of the measuring the difference in the pressure of the fluid on one side of differential pressure sensor 234 and pressure on the second side of differential pressure sensor 234. Differential pressure sensor is then capable of providing a signal that is proportional to the measured difference in pressure to the system controller. A valve 246 is disposed in second T-fitting 242 to control connection of second test line section 212b to differential pressure sensor 234.

A chemistry inlet line 252 is fluidly connected to first branch feeder line 124. A valve 254 is disposed in chemistry feed line 252 to control flow of fluid therethrough. A pressure sensor 256 is disposed within chemistry inlet line 252 for providing signals to the system controller indicative of the pressure of fluids therein. Chemistry inlet line 252 splits into two sections 252a, 252b that both connect to a chemistry-delivery system 400. Chemistry-delivery system 400, that will be described in greater detail below, is comprised of a chemistry housing 470 and a movable lid 520 that attaches to chemistry housing 470. Chemistry housing 470 of chemistry-delivery system 400 includes two separate compartments or receptacles 482, 484. Compartment 482 is dimensioned to receive a container containing a chemical reagent. Compartment 484 is dimensioned to receive a container that contains builder material to react with the chemical reagent in the first container to create a microbial deactivation fluid. As shall be described in greater detail below, lid 520 is designed to isolate the respective compartments when in a closed position.

Section 252b of chemistry inlet line 252 communicates with the container containing the builder material. Section 252a of chemistry inlet line 252 connects to the container holding the chemical reagent. A valve 258 is disposed within section 252a of chemistry inlet line 252 to control the flow of fluid therethrough.

Each compartment of chemistry housing 470 of chemistry-delivery system 400 is designed to have an outlet port formed at the upper edge thereof. A chemistry outlet line 262 connects chemistry-delivery system 400 to return line 162. Chemistry outlet line 262 has a first overflow line 262a and a second overflow line 262b. First overflow line 262a connects the upper portion of the first compartment of the housing to outlet line 262. Second overflow line 262b connects the upper portion of the second compartment of the housing to outlet line 262. A chemistry housing drain line 264 connects the bottom of chemistry housing 470 to chemistry outlet line 262. Chemistry housing drain line 264 has a first section 264a connected to the lowest part of the first compartment in chemistry housing 470, and a second section 264b is connected to the lowest part of the second compartment in chemistry housing 470. A valve 266 disposed within chemistry housing drain line 264 controls the flow of fluid from chemistry-delivery system 400. A drain line 272 connects to chemistry outlet line 262. A valve 274 is disposed in drain line 272 to control the flow of fluid therethrough. Downstream of drain line 272, a valve 276 is disposed in chemistry outlet line 262.

As shown in FIG. 4, a portion 252a of chemistry inlet line 252 is connected to chemistry outlet line 262. In this respect, portion 252a of chemistry inlet line 252 is disposed relative to two valves 254, 276 such that chemistry inlet line 252 is always in communication with chemistry outlet line 262 and ultimately, in connection with return line 162. In other words, a direct path is established between first branch feeder line 124 and chemistry outlet line 262. A connecting line 282 connects water inlet line 102 to chemistry inlet line 252. Two spaced-apart valves 284, 286 are disposed in connecting line 282. An air line 288 is connected to connecting line 282 between valves 284, 286. A direction check valve 289 is disposed in air line 288 to permit air flow only into connecting line 282.

Referring now to the drawer assembly shown in FIG. 4, an overflow line 292 is connected to plate 642 so as to communicate with the decontamination chamber. The other end of overflow line 292 is connected to a drain source. A check valve 293 is disposed within overflow line 292 to allow the flow of fluid out of the decontamination chamber, but to restrict the flow of any fluid into the decontamination chamber through overflow line 292. A sensor 294 is disposed within overflow line 292 downstream from directional check valve 293, to indicate when fluid is flowing therethrough. A make-up air line 296 is also connected to the decontamination chamber, as schematically illustrated in FIG. 3. A filter element 297 is disposed within make-up air line 296 to filter any air flowing into the decontamination chamber. In this respect, a directional check valve 298 is disposed within make-up air line 296 between filter element 297 and the decontamination chamber. Directional check valve 298 allows the flow of air into the decontamination chamber, but restricts the flow of air or fluid out of the decontamination chamber.

Filter Assembly 300

Figure 10:
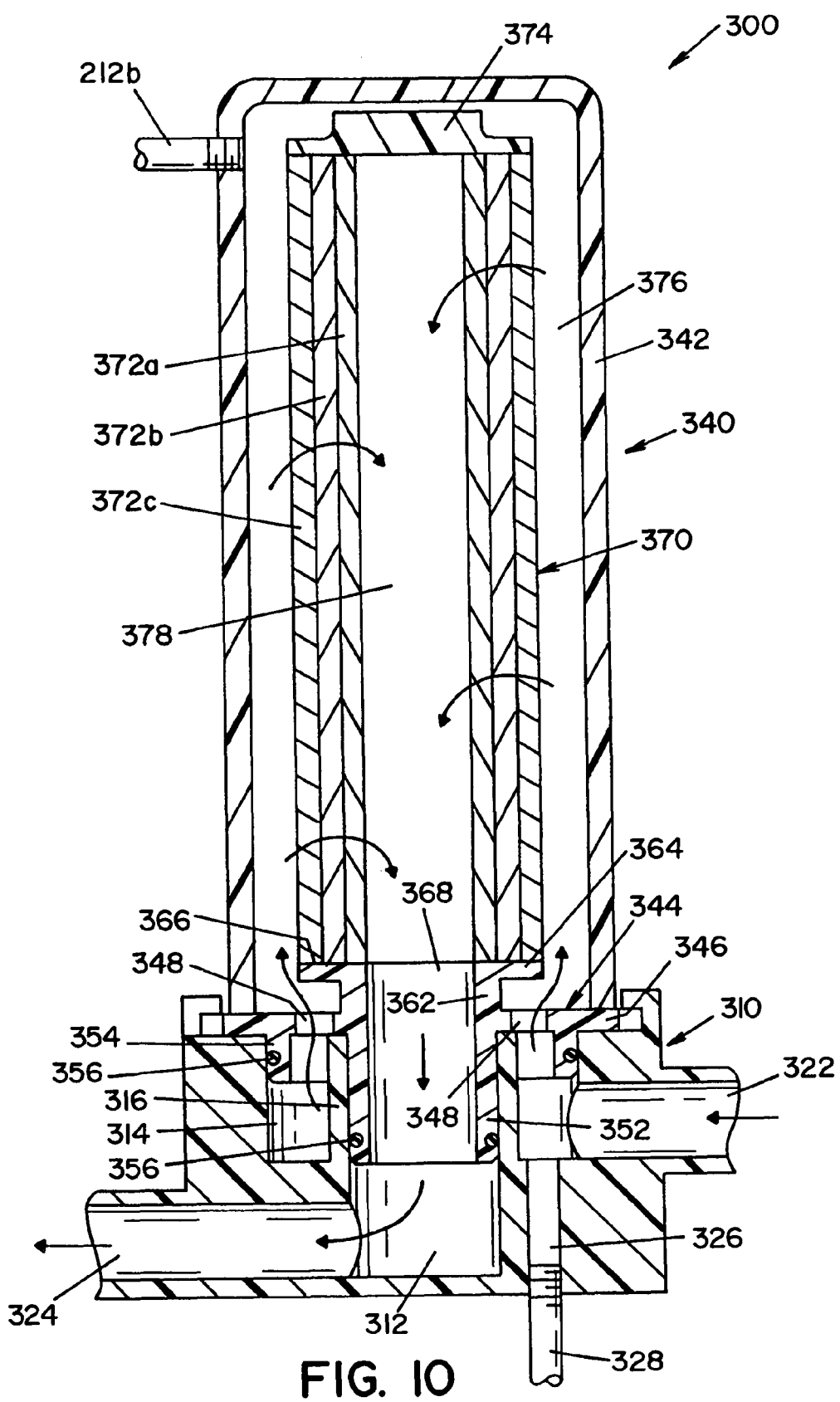
FIG. 10 is a sectional view of a filter element from the reprocessor shown in FIG. 1.

Referring now to FIG. 10, the filter assembly 300 is best seen. Filter assembly 300 is comprised of a support member 310 having a filter cartridge 340 attached thereto. Support member 310 has a central bore 312 formed therein. An annular slot 314 is formed in support member 310 around bore 316. Annular slot 314 is concentric to central bore 312 and defines an annular wall 316 within support member 310. A first passage 322 communicates with slot 314. A second passage 324 communicates with bore 312. Support member 310 is designed to be inserted into system feeder line 122 by conventional fasteners, such that first passage 322 defines an inlet port and second passage 324 defines an outlet port. A drain opening 326 extends from the bottom of support member 310 to annular slot 314. A drain conduit 328 is attached to drain opening 326.

Filter cartridge 340 includes a housing 342 and a base 344 that are dimensioned to contain an inner filter element 370. Base 344 is comprised of a mounting plate 346 having two annular walls 352, 354 that extend downward from the bottom of plate 346. The inner annular wall 352 is dimensioned to be received within bore 312, formed in support member 310. Outer annular wall 354 is dimensioned to engage the outer-most inner surface of annular slot 314. O-rings 356 are provided on outer surfaces of inner and outer walls 352, 354 to form a seal with surfaces of central bore 312 and annular slot 314, as illustrated in FIG. 10. An upper annular wall 362 extends from the upper surface of plate 346. The free end of wall 362 includes an outward-extending flange 364 that defines a planar upper surface 366. A central bore 368 extends through base 344, as illustrated in FIG. 10. Housing 342 is preferably attached to base 344 by means of ultrasonic welding.

A filter element 370 is mounted onto surface 366 of filter base 344. In the embodiment shown, filter element 370 has three layers 372a, 372b, 372c of filter media. As will be appreciated by those skilled in the art, each layer 372a, 372b, 372c filters a different size particle, with inner layer 372a having the highest filtering capability. A cap 374 is provided at the upper end of filter element 370. An outer annular chamber 376 is formed between the outer housing 342 and outer layer 372c of the filter media. A central cavity 378 is formed within filter element 370. Cavity 378 communicates with bore 312 in support member 310, which in turn communicates with feeder feed line 122. Filter cartridge 340 may be attached to support member 310 in a number of different ways. In the embodiment shown, a bayonet-type lock arrangement is shown.

Test line 212b is attached to housing 342, and it communicates with the annular chamber 376 formed therein. Openings 348 are formed through plate 346 of base 344 to permit the flow of fluid therethrough. Openings 348 are positioned to allow annular chamber 376 to communicate with slot 314, as shown in FIG. 10. As illustrated by arrows in FIG. 10, water or a decontamination fluid from system feed line 122 flows into first passage 322 (the inlet port) of support member 310 and upwards through opening 348 in plate 346 into annular chamber 376. The water or decontamination fluid then flows through filter element 370, where the water or fluid is filtered as it passes through layers 372a, 372b, 372c of filter media. The water or fluid then flows down through cavity 378 and central bore 312 in support member 310 and, ultimately, to second passage 324 (the outlet port) into fluid feed line 122.

Chemistry-Delivery System 400

Figure 11:
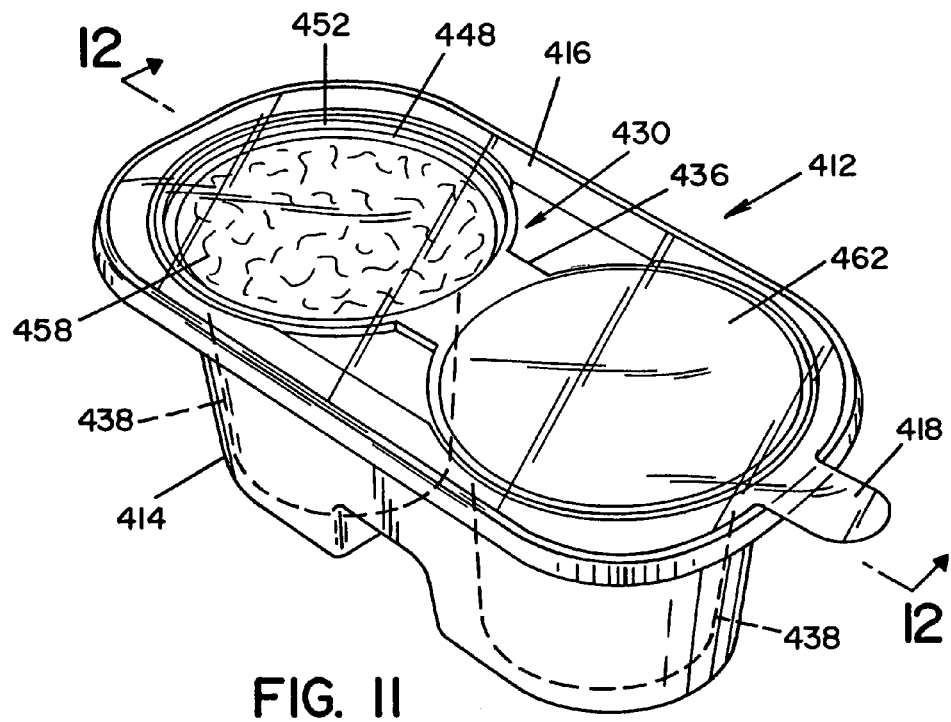
FIG. 11 is a sealed package containing a chemistry-holding device that is used in the reprocessor shown in FIG. 1.

Referring now to FIGS. 11-17, the chemistry-delivery system 400 is best seen. Chemistry-delivery system 400 is designed to use a chemistry-holding device 430. FIG. 11 shows a chemistry-storage package 412 containing a chemistry-holding device 430. Chemistry-storage package 412 is comprised of a molded base 414 having a peel-away lid or cover 416. Base 414 is generally comprised of an integrally molded polymer material. Cover 416 is preferably a polymer film that is attached to base 414, so as to be easily peeled away. A tab 418 extends from, and is integrally formed as part of cover 416 to facilitate removal of cover 416 from base 414. Chemistry-storage package 412 is dimensioned to loosely contain chemistry-holding device 430.

Figure 12:
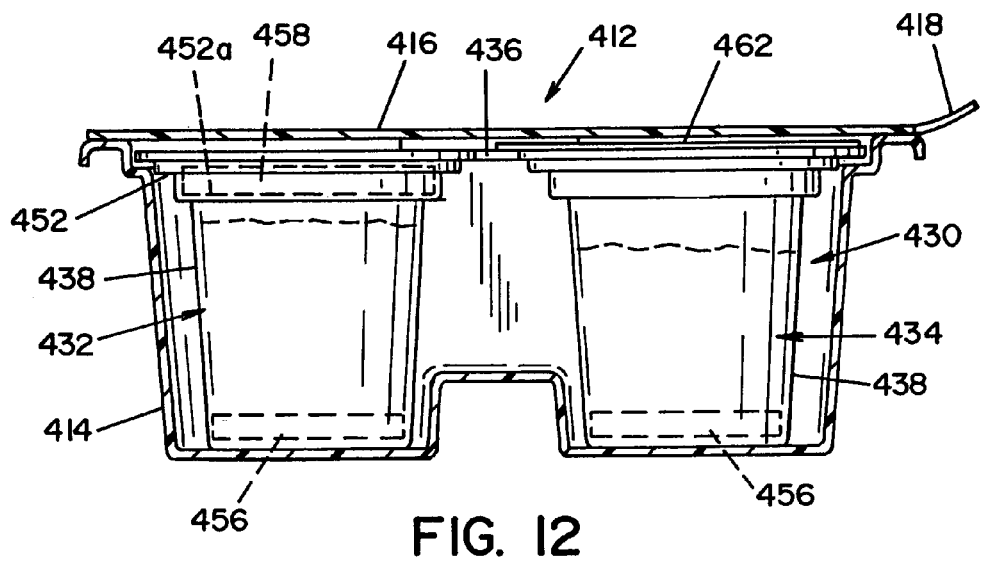
FIG. 12 is a sectional view taken along lines 12-12 of FIG. 11.

Referring now to FIG. 12, chemistry-holding device 430 is best seen. Chemistry-holding device 430 is basically comprised of two side-by-side containers 432, 434 that are connected along their upper surfaces by a bridge portion 436. Both containers 432, 434 are slightly conical in shape and include a tubular body 438 that is defined by an annular wall 442. The lower end of each wall 442 includes an inwardly turned edge 444 that defines an opening 446 at the bottom of each container 432, 434. The upper end of each container 432, 434 defines an opening 448. The upper end of container 432, 434 includes an outward extending, stepped flange 452. Stepped flange 452 defines an annular, upward-facing surface 452a.

A filter element 456 is disposed at the bottom of each container 432, 434. Filter element 456 is essentially a flat disk that is dimensioned to have an outer peripheral shape, matching the inner profile of each container 432, 434. In this respect, each filter element 456 is dimensioned to be snugly received in the bottom of container 432, 434, with the outer edge of filter element 456 resting on upward-facing surface defined by inwardly extending edge 444.

A second filter element 458 is provided in container 432 to close the opened upper end thereof. Like filter element 456, filter element 458 is a flat disk that is dimensioned to have an outer peripheral shape, matching the inner profile of stepped flange 452 of wall 442. In this respect, in the embodiment shown, filter element 458 is circular in shape and is dimensioned to be snugly received within stepped-flange 452 of container 432, with filter element 458 resting on annular surface 452a defined by stepped flange 452.

A thin polymer layer 462 is provided to close the opened upper end of container 434. Polymer layer 462 is dimensioned to rest upon annular surface 452a defined by stepped flange 452 of container 434. Filter elements 456, 458 and polymer layer 462 are preferably ultrasonically welded to containers 432, 434.

Filter elements 456, 458 are formed of a filter material that is impermeable to the dry reagents to be contained within containers 432, 434, but is permeable to water and to dissolved reagents. Filter element 456 is preferably dimensioned to filter particles larger than 50 microns ($\mu m$) and, more preferably, to filter particles of about 10 microns ($\mu m$). Suitable filter materials include polypropylene, polyethylene, nylon, rayon, rigid porous media (such as POREX™), expanded plastic or other porous plastic, fabric, felt, mesh, and analogous materials. The filtering capabilities of the selected filtering material are related to the dry reagent contained within respective container 432, 434. In a preferred embodiment, filter element 456 is preferably formed of an ethylene-based polymer, such as polypropylene or polyethylene. Container 432 is dimensioned to contain a predetermined amount of acetylsalicylic acid, i.e., aspirin.

Container 434 is dimensioned to receive builder components that contain a per-salt, preferably sodium perborate. The builder components are supplied at sufficient amounts to react with the acetylsalicylic acid to generate peracetic acid at a concentration of 1,500 ppm or better with the volume of water to be used in the system in which chemistry-delivery system 400 is to be used. The sodium perborate generates hydrogen peroxide, which, in combination with acetylsalicylic acid as an acetyl donor, forms peracetic acid.

The use of powdered reagents that react in a common solvent to generate chlorine gas, hydrogen peroxide, hypochlorous acid, hypochlorides, or other strong oxidants which have biocidal effects is also contemplated.

Container 434 also preferably includes various chemistries, such as buffers, inhibitors and wetting agents. Preferred copper and brass corrosion inhibitors include azoles, benzoates, and other five-member ring compounds, benzotriazoles, tolytriazoles, mercaptobenzothiazole, and the like. Other anti-corrosion buffering compounds include phosphates, molybdates, chromates, dichromates, tungstates, vanadates, and other borates, and combinations thereof. These compounds are effective for inhibiting steel and aluminum corrosion. For hard water in which calcium and magnesium salts may tend to precipitate, a sequestering reagent, such as sodium hexametaphosphate, is also included.

As illustrated in FIG. 12, chemistry-storage package 412 is dimensioned to receive the chemistry-holding device 430, so as to allow storage and shipping of the chemistry-holding device 430 in a sealed package.

Figure 13:
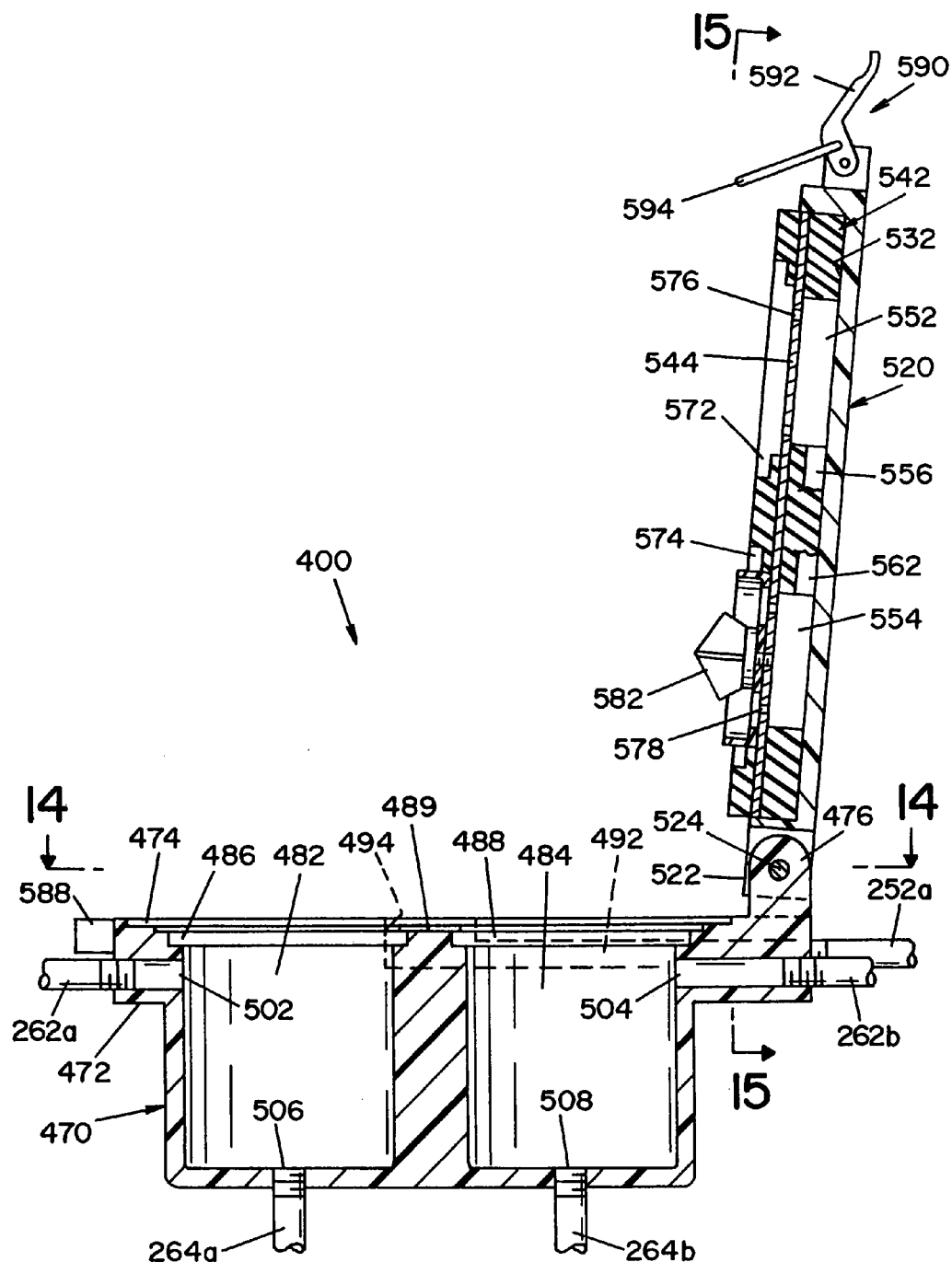
FIG. 13 is a sectional view of a chemistry-delivery system used in the reprocessor shown in FIG. 1, showing the chemistry-delivery system in an open position.
Figure 14:
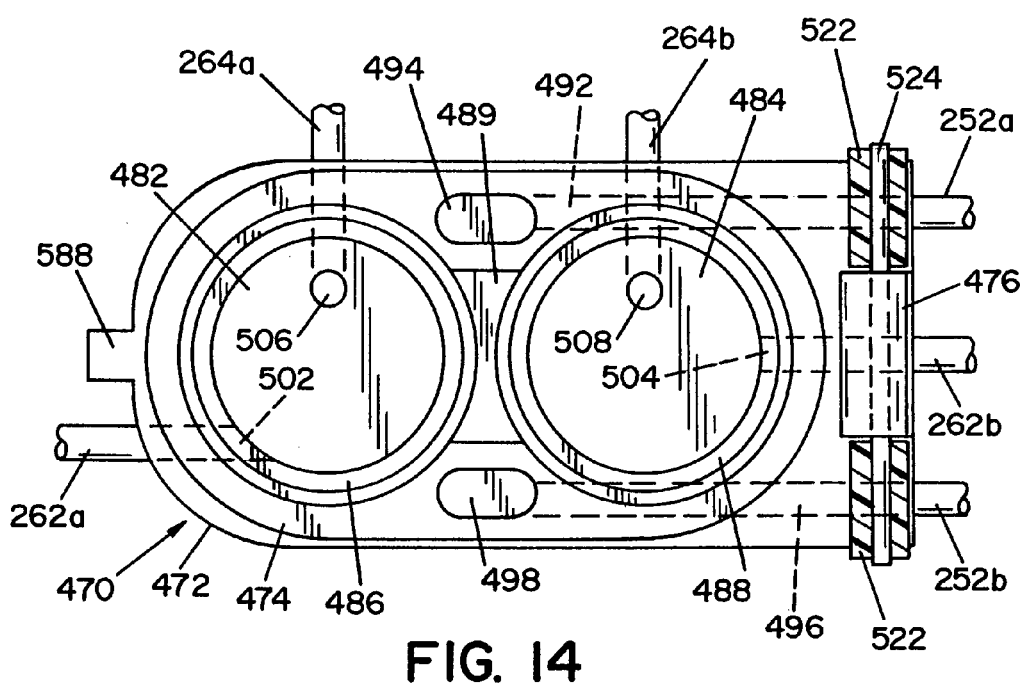
FIG. 14 is a sectional view taken along lines 14-14 of FIG. 13.
Figure 15:
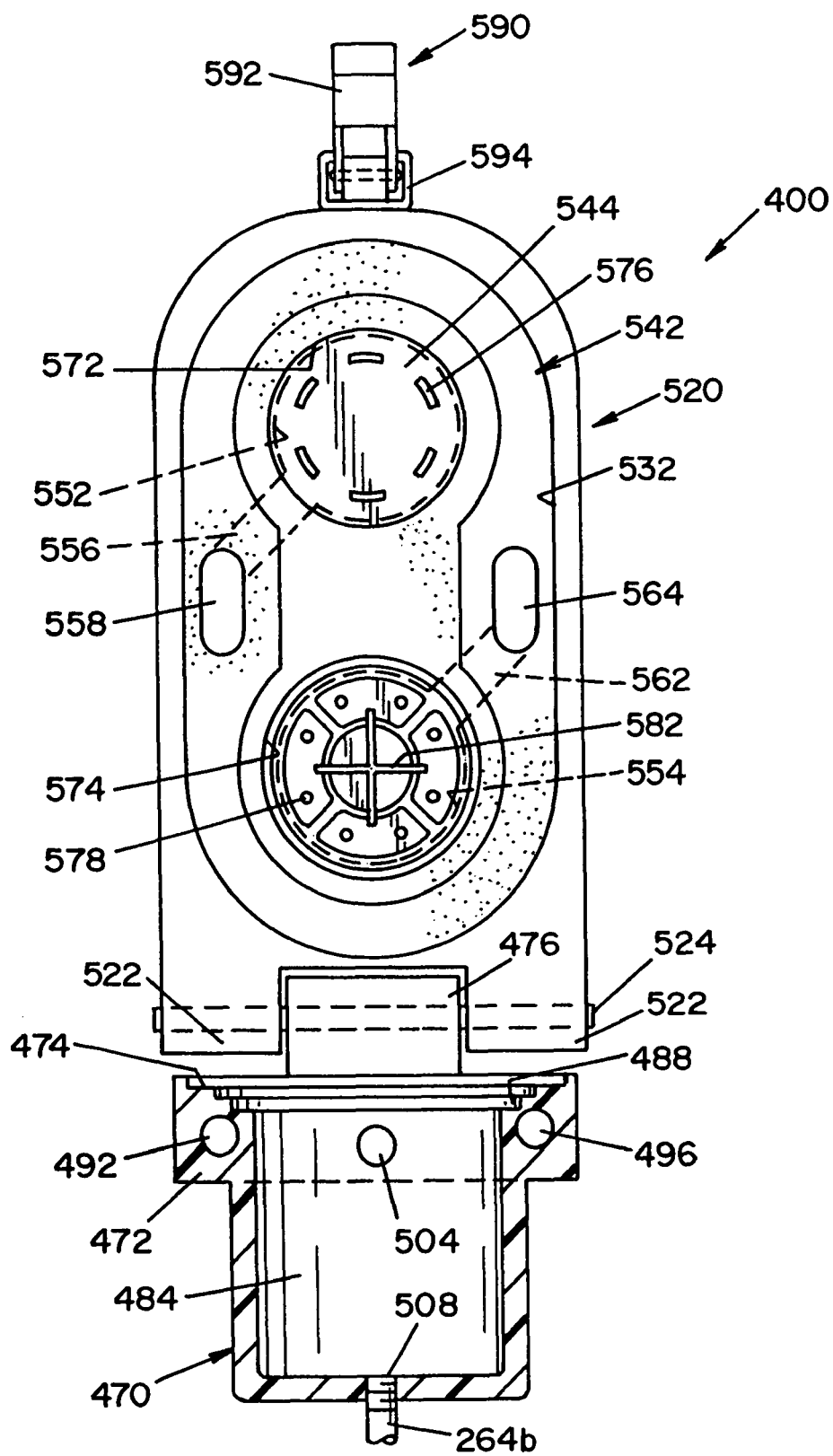
FIG. 15 is a sectional view taken along lines 15-15 of FIG. 13.
Figure 16:
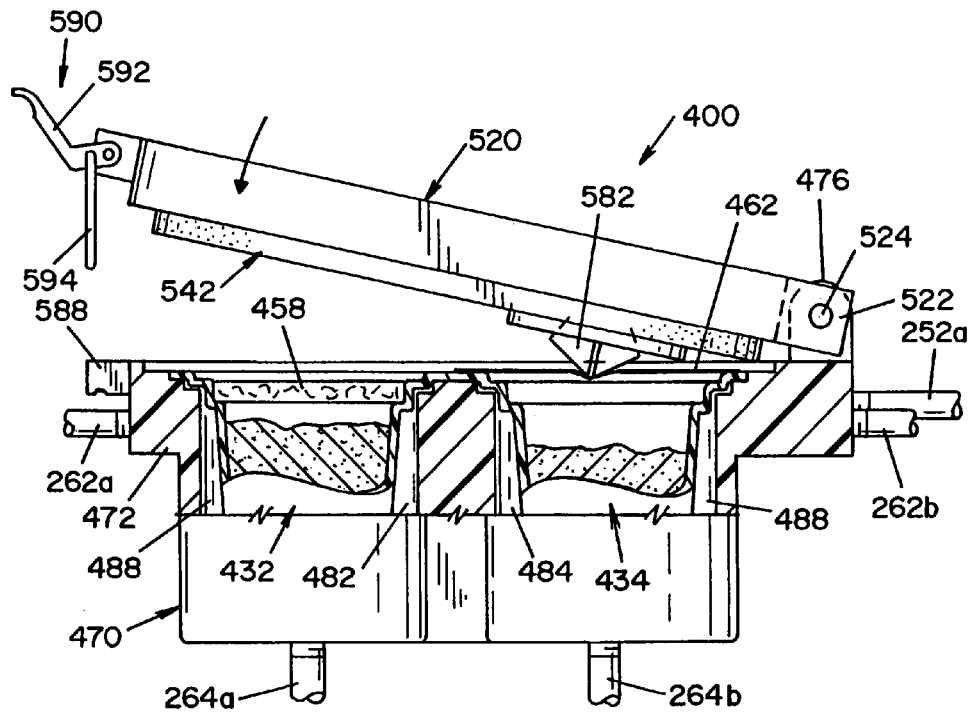
FIG. 16 is a partially sectioned, side-elevational view of the chemistry-delivery system, showing a chemistry-holding device disposed therein.
Figure 17:
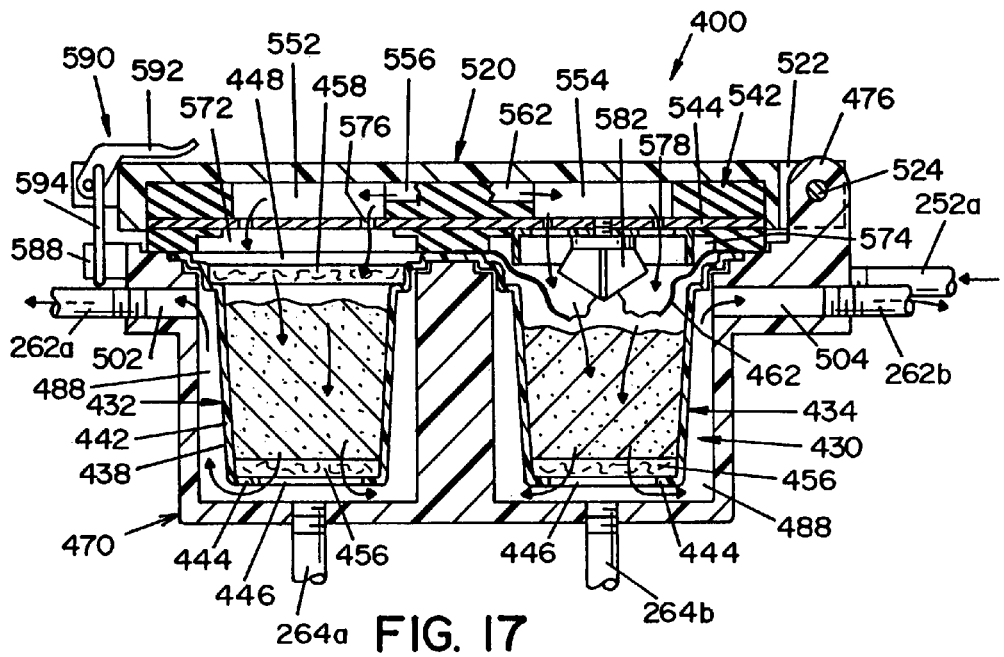
FIG. 17 is a sectional view of the chemistry-delivery system in operation.

Referring now to FIGS. 13-17, chemistry-delivery system 400 is best seen. Chemistry-delivery system 400 is comprised of an elongated, oblong housing 470 having a lid 520 that is pivotally attached thereto. An outward extending collar 472 extends around the periphery of housing 470. As best seen in FIGS. 13, and 14, an obround recess 474 is formed in the upper surface of housing 470. Housing 470 includes two spaced-apart, side-by-side compartments or receptacles 482, 484 that are dimensioned to receive, respectively, containers 432, 434 of chemistry-holding device 430. Compartments 482, 484 extend from recess 474 into housing 470. Compartments 482, 484 are generally cylindrical in shape and slightly larger than containers 432, 434 to define a space 488 around the sides and bottoms of containers 432, 434, as best illustrated in FIG. 17.

Stepped regions 486, 488 are formed at the upper ends of compartments 482, 484. Stepped regions 486, 488 are dimensioned to receive stepped flanges 452 on containers 432, 434 and are formed below the surface of recess 474, as best seen in FIG. 13. A slot 489 is formed in recess 474 between compartments 482, 484. Slot 489 is dimensioned to receive bridge portion 436 of chemistry-holding device 430.

A first inlet passage 492 is formed in collar 472 of housing 470. Inlet passage 492 extends from one end of housing 470 to an elongated opening 494 defined on the upper surface of recess 474 of housing 470. A second inlet passage 496 is formed into housing 470 and communicates with a second oblong opening 498 on the surface of recess 474 of housing 470. First inlet passage 492 is connected to branch 252a of chemistry-inlet line 252 of fluid-circulation system 100. Second inlet passage 496 is connected to branch 252b of chemistry-inlet line 252. Overflow ports 502, 504 are provided, respectively, at the upper portions of compartments 482, 484. Overflow port 502 in compartment 482 is connected to overflow line 262a of fluid-circulation system 100. Overflow port 504 in compartment 484 is connected to overflow line 262b of fluid-circulation system 100. Drain openings 506, 508 are provided at the bottom of compartments 482, 484, respectively. Opening 506 in the bottom of compartment 482 is connected to section 264a of chemistry-housing drain line 264. Opening 508 in the bottom of compartment 484 is connected to section 264b of chemistry-housing drain line 264.

Lid 520 is basically an elongated plate having an outer peripheral shape corresponding to the shape of collar 472 of housing 470. One end of lid 520 includes two spaced-apart arms 522 that are dimensioned to straddle a support bracket 476 on the housing 470. A pin 524, extending through spaced-apart arms 522 and support bracket 476, pivotally mounts lid 520 to housing 470. Lid 520 includes an obround recess in the lower surface thereof. Recess 532 has the same dimensions as recess 474 in housing 470. A seal element 542 is disposed in recess 532 in lid 520. A flat metallic plate 544 is molded within seal element 542, as best seen in FIGS. 13 and 17. Two spaced-apart, circular cavities 552, 554 are formed in seal element 542 to one side of plate 544. Cavities 552, 554 are formed between plate 544 and lid 520. A channel 556 extends from circular cavity 552 and communicates with an opening 558 that extends through seal element 542. Opening 558 is disposed to be in registry with opening 494 in housing 470 when lid 520 is in a closed position, as shall be described in greater detail below. Similarly, a channel 562 extends from circular cavity 554 and communicates with an opening 564 that extends through seal element 520. Opening 564 is disposed to be in registry with opening 498 in housing 470 when lid 520 is in a closed position. Seal element 542 is preferably integrally formed of a resilient material. Circular openings 572, 574, in the underside of seal element 542 expose plate 544. Openings 572, 574 are in registry with circular cavities 552, 554 on the opposite side of plate 544. A circular pattern of slot-shaped apertures 576 are formed through plate 544, such that cavity 552 communicates with opening 572. A circular pattern of circular apertures 578 are formed through plate 544, such that cavity 554 communicates with opening 574. Apertures 576, 578 are dimensioned to define spray orifices for spraying fluid into compartments 482, 484 when lid 520 is attached to housing 470. In this respect, openings 572, 574 are disposed on lid 520 to align with compartments 482, 484, respectively, when lid 520 is in a closed position as shown in FIG. 17. Apertures 576 are dimensioned such that the total cross sectional area of apertures 576 are between about 1% and about 10% of the total cross sectional area of apertures 578. In one embodiment, the total cross sectional areas of apertures 576 are between about 3% and about 7% of the total cross sectional area of apertures 578. In another embodiment, the total cross sectional are of apertures 576 are about 5% of the total cross sectional area of apertures 578.

A blade element 582 is attached to plate 544 within opening 574. Blade element 582 is disposed to be in registry with compartment 484 in housing 470. A tab 588 extends to one side of housing 470. Lid 520 includes a latch assembly 590, including a latch handle 592 and a latch ring 594 dimensioned to capture tab 588 and pull lid 520 into sealing engagement with housing 470. In this respect, lid 520 is movable between a first open position, as illustrated in FIG. 13, and a second closed position, as illustrated in FIG. 17. As shown in FIG. 17, blade element 582 is dimensioned to penetrate plastic cover layer 462 on the second container 434.

Drawer Assembly 600

Figure 18:
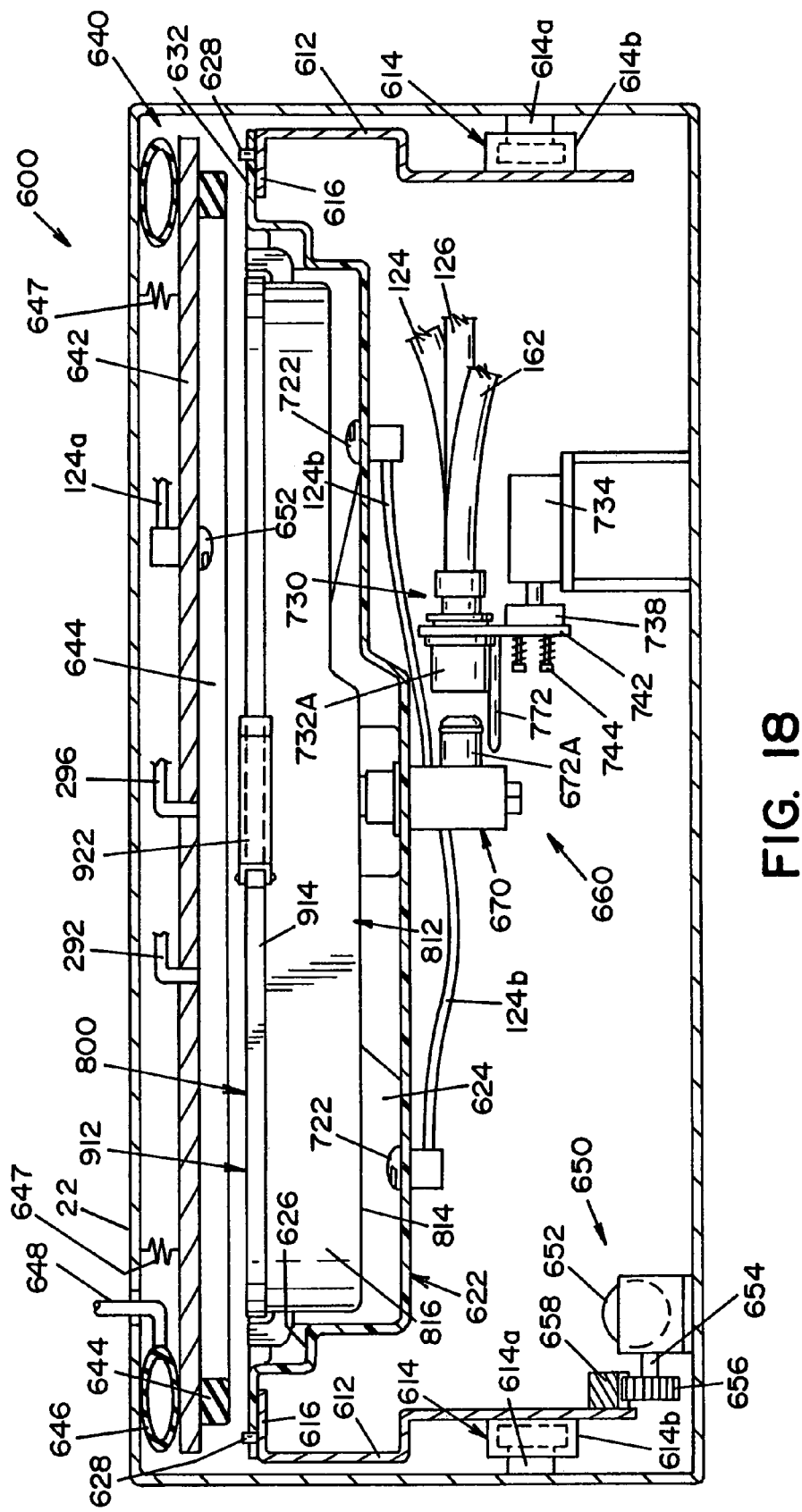
FIG. 18 is a cross-sectional view of a drawer assembly from the apparatus show in FIG. 1.

Referring now to FIGS. 18-23, drawer assembly 600 is best seen. Drawer assembly 600 includes two spaced-apart side panels 612. Each side panel 612 has a drawer slide 614 associated therewith. Drawer slide 614 has a first section 614a attached to housing structure 22 and a second section 614b attached to a side panel 612. Each side panel 612 has an inwardly extending flange 616 at the upper end thereof. Drawer tray 622 is dimensioned to rest upon inward-extending flanges 616. Drawer tray 622 is generally comprised of a flat panel having a recessed cavity 624 formed therein. Cavity 624 has a pre-determined contour dimensioned to receive instrument container 800. As illustrated in FIG. 18, a ledge 626 is formed about the peripheral edge of cavity 624 to receive instrument container 800. Drawer tray 622 is positioned on inwardly extending flanges 616 of side panels 612 by cylindrical posts 628. Drawer tray 622 has a generally planar surface 632, best seen in FIG. 2, that surrounds cavity 624. A front door panel 634, best seen in FIGS. 1 and 2, is attached to side panels 612. A control button 636, for controlling movement of drawer assembly 600, is mounted to front panel 634.

A drawer sealing assembly 640 is disposed above drawer tray 622. Drawer sealing assembly 640 includes a plate 642 that is disposed above drawer tray 622. The dimensions of plate 642 generally correspond to the dimensions of drawer tray 622. A static seal 644 is disposed on the lower surface of plate 642. Static seal 644 is disposed about the periphery of cavity 624 in drawer tray 622, so as to engage flat upper surface 632 of drawer tray 622. It is contemplated that the bottom surface of plate 642 can be generally hemispherical in shape within the boundary defined by static seal 644. In this respect, the highest point of the hemispherical portion of the bottom side of plate 642 is higher than any point at which static seal 644 contacts plate 642. An inflatable bladder 646 is disposed between plate 642 and housing structure 22, as illustrated in FIG. 18. An air line 648 is connected to bladder 646 to inflate and deflate the same. When inflated, air bladder 646 is operable to force plate 642 downward toward drawer tray 622, wherein static seal 644 engages upper surface 632 of drawer tray 622 to form a seal about cavity 624 formed therein. When plate 642 is sealed against surface 632 of drawer tray 622, cavity 624 within drawer tray 622 defines a sealed decontamination chamber. A plurality of springs 647 are connected at one end to the upper side of plate 642 and at the other end to housing structure 22. Springs 647 are tension springs that bias plate 642 and static seal 644 away from the planar portion of drawer tray 622.

Overflow line 292 and make-up air line 296 are attached to plate 642 and extend therethrough. In an alternative embodiment of seal plate 642 as described above, where the bottom side of seal plate 642 is hemispherical in shape, overflow line 292 is located at the highest point of the hemispherical portion of the bottom side of seal plate 642. In this respect, when plate 642 is in a sealing position against drawer tray 622, overflow line 292 and make-up air line 296 are in communication with the decontamination chamber defined between plate 642 and drawer tray 622. Section 124a of first branch feeder line 124 is also attached to plate 642, as illustrated in FIG. 18. Section 124a of first branch feeder line 124 connects to a spray nozzle 652 disposed on the bottom side of plate 642.

A drawer drive assembly 650 is provided to move drawer tray 622 between a closed position shown in FIG. 1 and an open position shown in FIG. 2. Drive assembly 650 is comprised of a drive motor 652 connected to housing structure 22. In a preferred embodiment, drive motor 652 is an electric motor. A pinion gear 656 is attached to output shaft 654 of drive motor 652. Pinion gear 656 engages a rack 658 on side panel 612 of drawer assembly 600. As best seen in FIGS. 2 and 3, drawer slides 614 and rack 658 on side panel 612 of drawer assembly 600 are disposed so as to move drawer tray 622 at an angle relative to horizontal. In the embodiment shown, drawer tray 622 moves within a plane that is approximately 20° down from horizontal.

Connector assembly 660 is provided to allow the lines from fluid circulation system 100 to be connected to, and disconnected from, drawer assembly 600, so as to allow the opening and closing of drawer tray 622. Connector assembly 660 is comprised of a manifold section 670, that is mountable to drawer tray 622 and is movable therewith, and a platen section 730, that is movable into and out of engagement with manifold section 670. Manifold section 670 is attached to the bottom of drawer tray 622 and has a plurality of male connectors 672A, 672B, 672C extending to one side thereof. The platen section 730 includes a plurality of female connectors 732A, 732B, 732C extending therefrom. Female connectors 732A, 732B, 732C are dimensioned to mate with male connectors 672A, 672B, 672C. Platen section 730 is operable to connect with and to disconnect from manifold section 670 when drawer assembly 600 is in a closed position, so as to connect drawer tray 622 to fluid circulation system 100.

Figure 19:
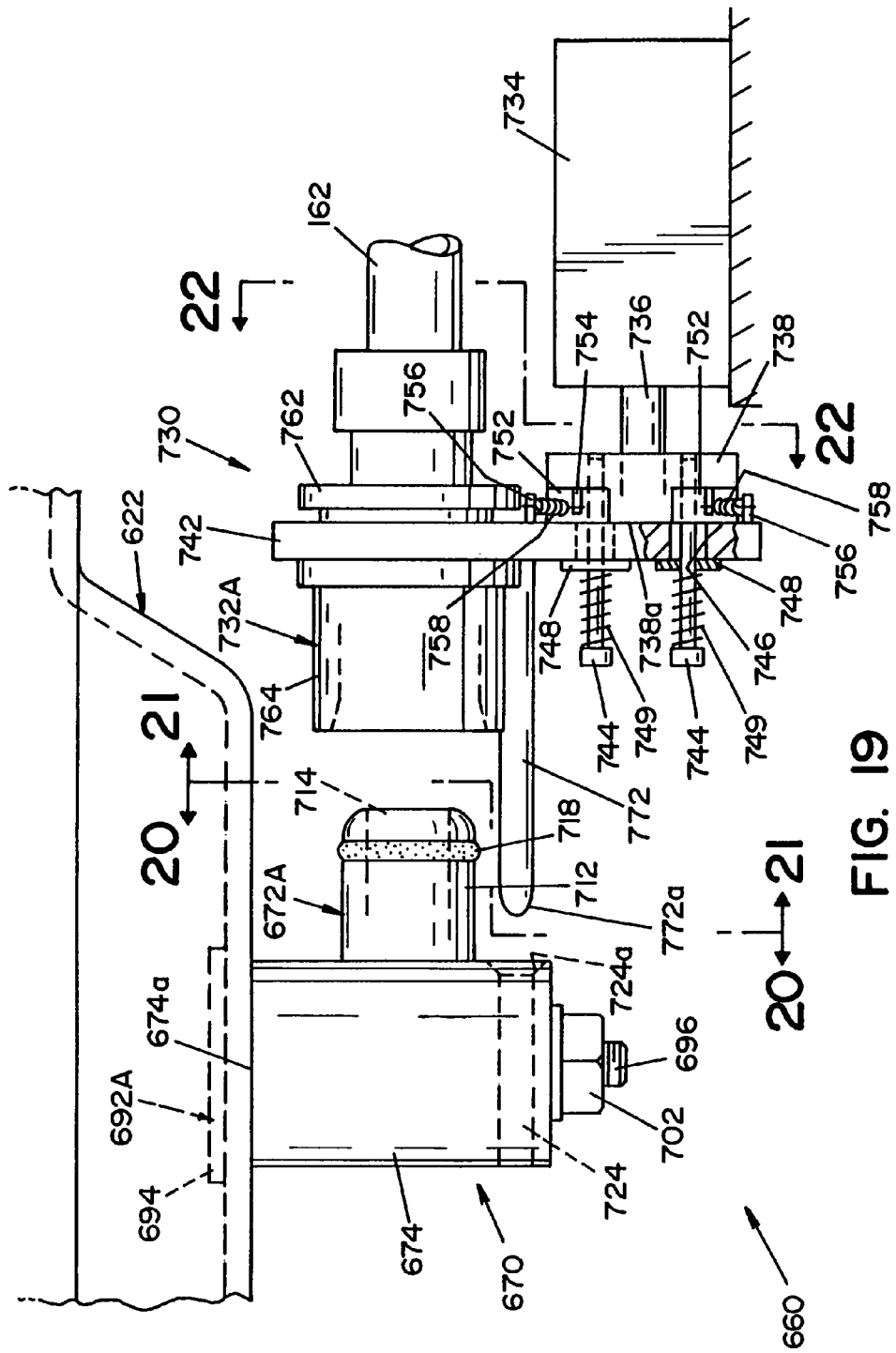
FIG. 19 is an enlarged view, showing a connector assembly for the drawer assembly show in FIG. 18.
Figure 20:
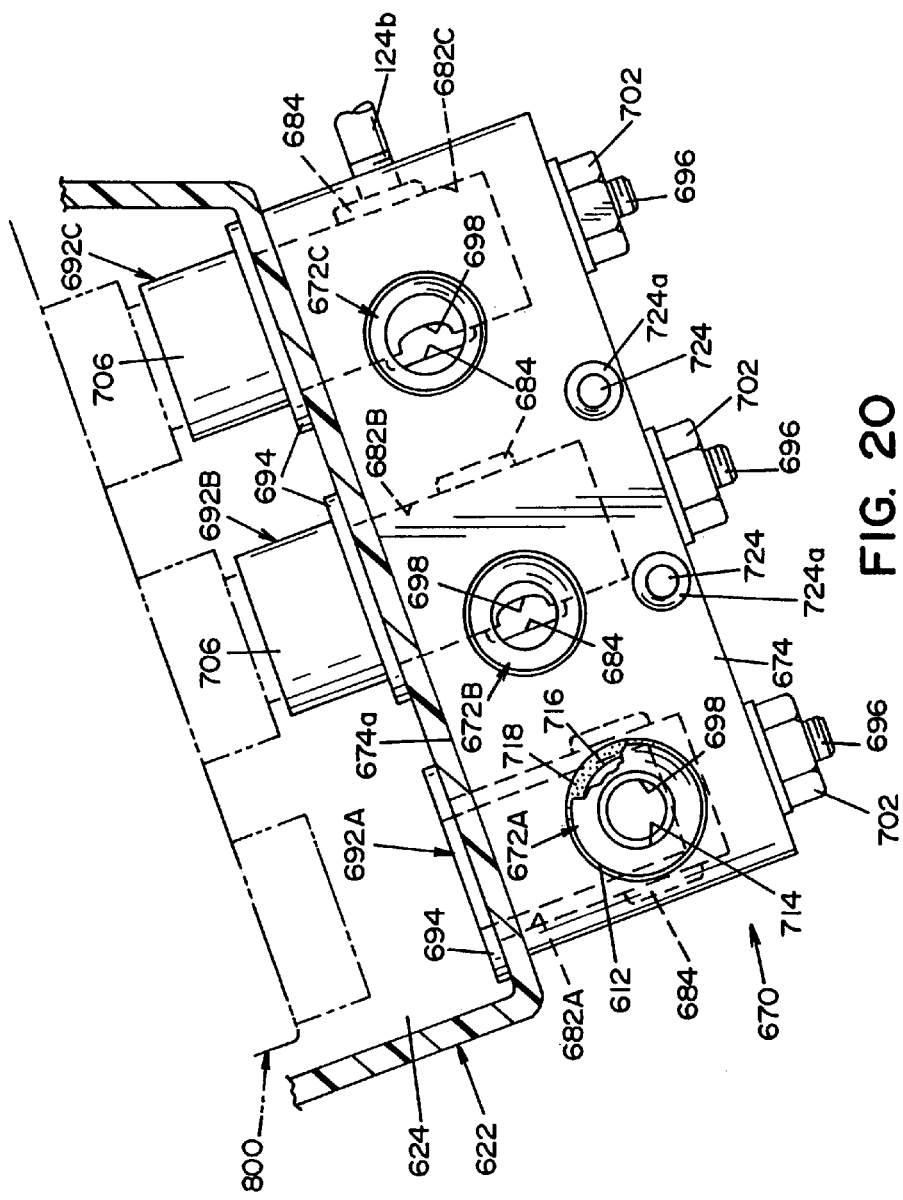
FIG. 20 is a sectional view taken along lines 20-20 of FIG. 19.
Figure 23:
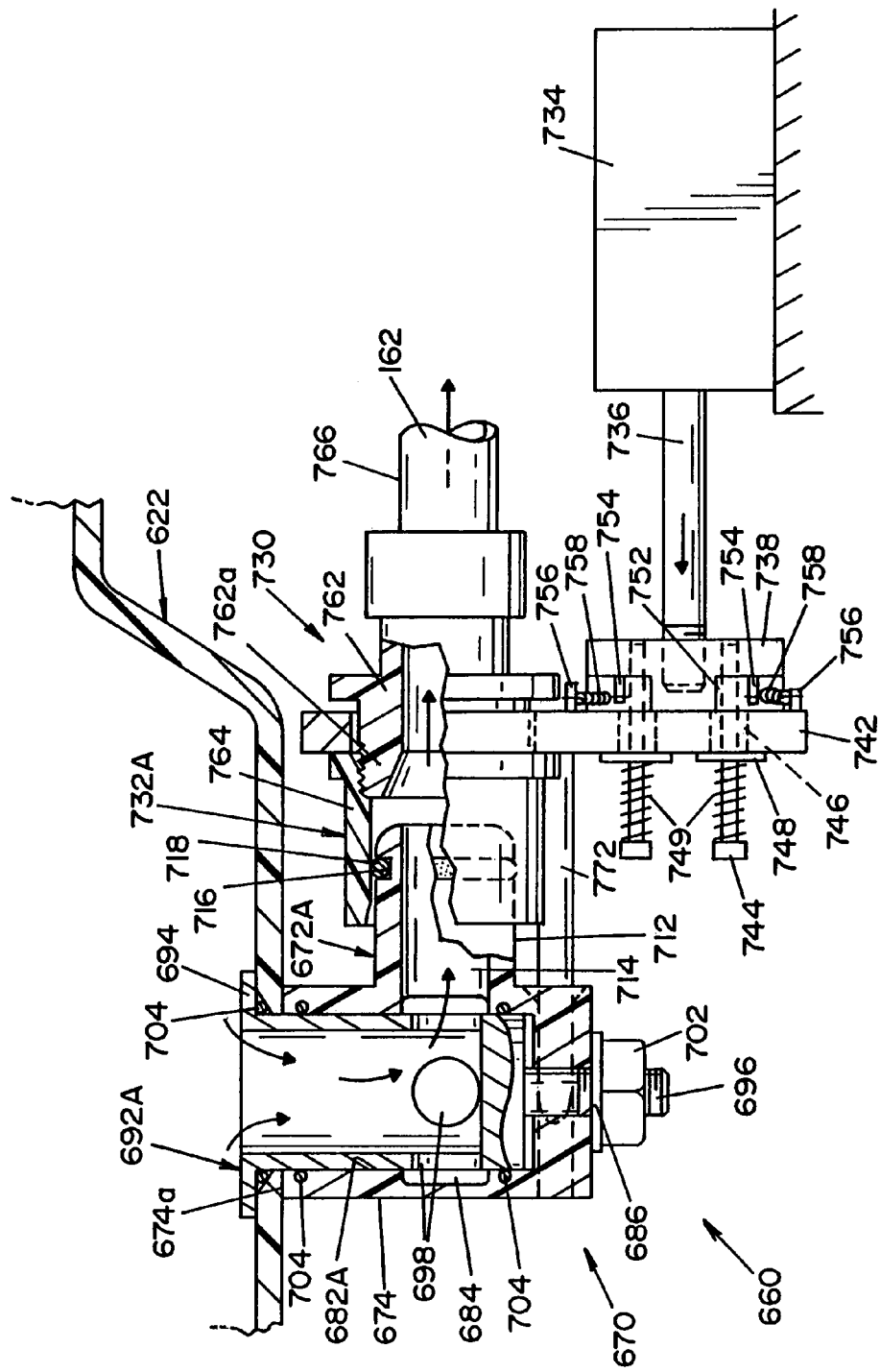
FIG. 23 is a partially sectioned view of the connector assembly shown in FIG. 19.

Referring now to FIGS. 19, 20, and 23, manifold section 670 is best seen. Manifold section 670 is comprised of a block 674 having a flat surface 674a dimensioned to engage the under side of drawer tray 622. Three bored openings extend into block 674 from flat surface 674a. Bored openings define cylindrical cavities 682A, 682B, 682C as best seen in FIG. 23 that shows cavity 682A. An annular groove 684 is formed in the inner surface of each cylindrical cavity 682A, 682B, 682C near the lower end thereof. A cylindrical aperture 686 axially aligned with each cylindrical cavity 682A, 682B, 682C and extends through the bottom of block 674. Aperture 686 has a smaller diameter than cylindrical cavity 682A, as illustrated in FIG. 23.

Each cylindrical cavity 682A, 682B, 682C is dimensioned to receive an insert 692A, 692B, 692C, respectively. In the embodiment shown, insert 692A, best seen in FIG. 23, is a drain insert and is disposed within cylindrical cavity 682A. Inserts 692B, 692C, best seen in FIG. 20, are connector inserts and are disposed in cylindrical cavities 682B, 682C, respectively. Each insert 692A, 692B, 692C is a tubular structure having a closed lower end and an opened upper end. An annular flange 694 extends outwardly from the upper end each insert 692A, 692B, 692C, as illustrated in FIG. 20. A threaded rod 696 extends from the bottom of each insert 692A, 692B, 692C. Rod 696 is dimensioned to extend through aperture 686 in the bottom of manifold block 674. A plurality of openings 698 is formed in the sidewall of the inserts 692A, 692B, 692C.

As shown in FIG. 23, each insert 692A, 692B, 692C is dimensioned to be disposed within its respective cylindrical cavity 682A, 682B, 682C in manifold block 674 with flange 694 disposed on the upper, inner surface of drawer tray 622. Conventional fastener nuts 702 on threaded rods 696 are tightened to draw inserts 692A, 692B, 692C down into manifold block 674 and force upper, planar surface of manifold block 674 into engagement with the lower, outer surface of drawer tray 622, thereby capturing drawer tray 622 between flanges 694 and block 674. A plurality of o-rings 704 is disposed between inserts 692A, 692B, 692C and drawer tray 622 and manifold block 674 to form a fluid-tight seal between the inserts 692A, 692B, 692C and drawer tray 622 and manifold block 674. As illustrated in FIG. 23, apertures 698 in inserts 692A, 692B, 692C are disposed to be in communication with annular grooves 684 formed within surface of cylindrical cavities 682A, 682B, 682C in manifold block 674.

In FIG. 23, drain insert 692A is shown. Connector inserts 692B, 692C, shown in FIG. 20, are similar in all respects with the exception that connector inserts 692B, 692C include an upwardly extending annular collar 706 that defines female inlet fittings, as shall be described in greater detail below.

As mentioned above, male connectors 672A, 672B, 672C extend to one side of block 674. Each connector 672A, 672B, 672C is essentially identical and, therefore, only one shall be described in detail. Male connector 672A, best seen in FIG. 23, is comprised of a cylindrical body 712 having an inner passage 714 extending therethrough. Body 712 is oriented such that passage 714 is aligned and communicates with annular groove 684 in cylindrical cavity 682A. Similarly, passage 714 in body 712 of male connector 672B communicates with annular groove 684 in cylindrical cavity 682B, and passage 714 in body 712 of male connector 672C communicates with annular groove 684 in cylindrical cavity 682C. An annular channel 716 is formed in outer surface of each body 712 to receive o-ring 718, as best illustrated in FIG. 23.

Manifold section 670 and inserts 692A, 692B, 692C may be formed of a metal or polymer material. In a preferred embodiment, manifold section 670 is formed of a high-strength polymer material. Inserts 692A, 692B, 692C are formed of a metal such as, by way of example and not limitation, stainless steel.

As best seen in FIG. 20, a plurality of distribution lines 124b are connected to manifold block 674 and communicate with annular groove 684 associated with cylindrical cavity 682C. Distribution lines 124b are connected to a plurality of spray nozzles 722 disposed on the upper, inner surface of drawer tray 622, as best seen in FIG. 18.

As indicated above, cavity 624 in drawer tray 622 has a pre-determined configuration. Because drawer tray 622 is oriented at an angle, manifold block 674 is oriented such that drain insert 692A is disposed at the lowest-most portion of drawer tray 622, as schematically illustrated in FIG. 4.

Manifold block 674 includes spaced-apart locating openings 724, best seen in FIG. 20. Locating openings 724 have counter-sunk leading edges 724a, best illustrated in FIG. 19.

Figure 21:
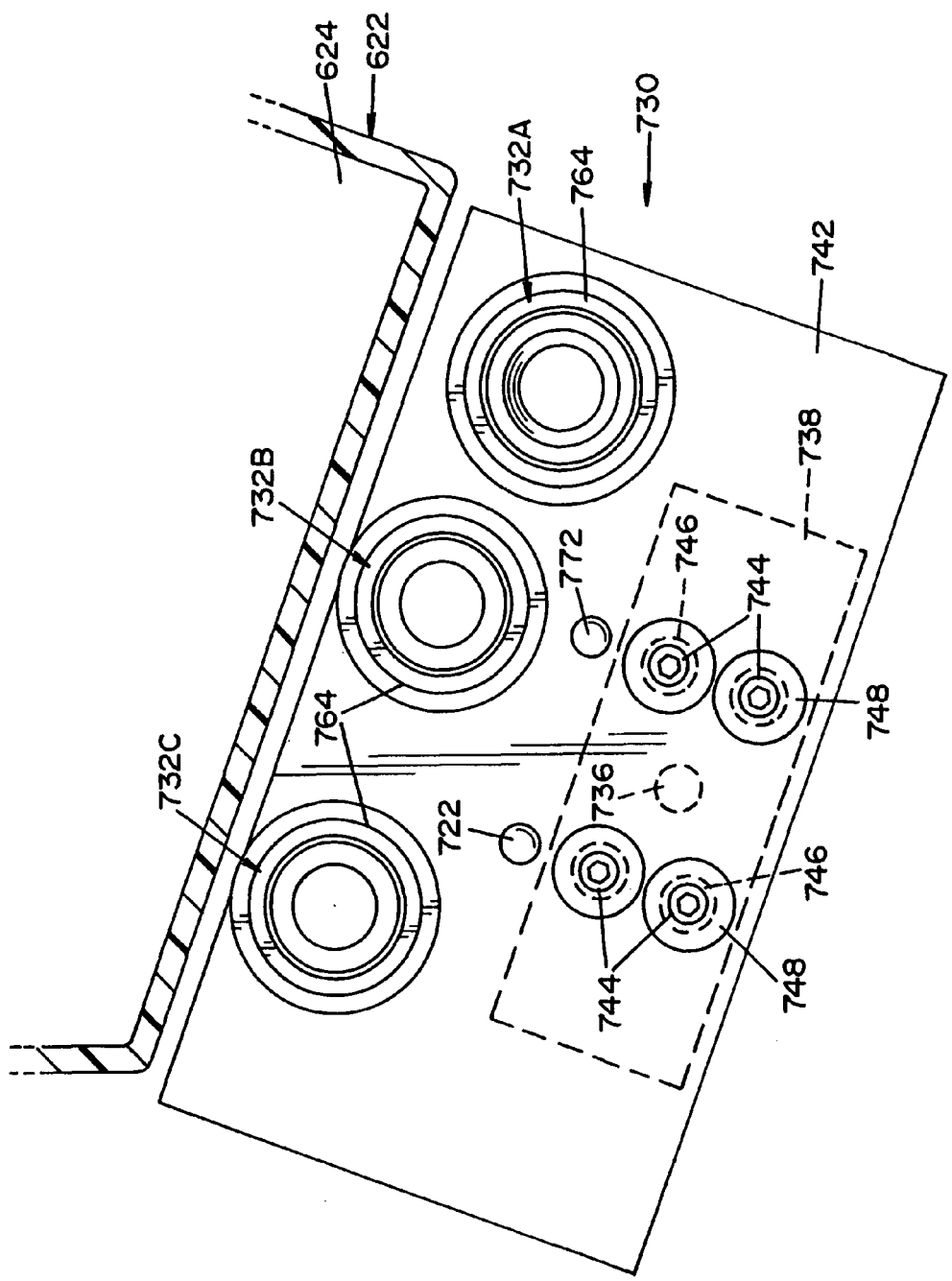
FIG. 21 is a sectional view taken along lines 21-21 of FIG. 19.
Figure 22:
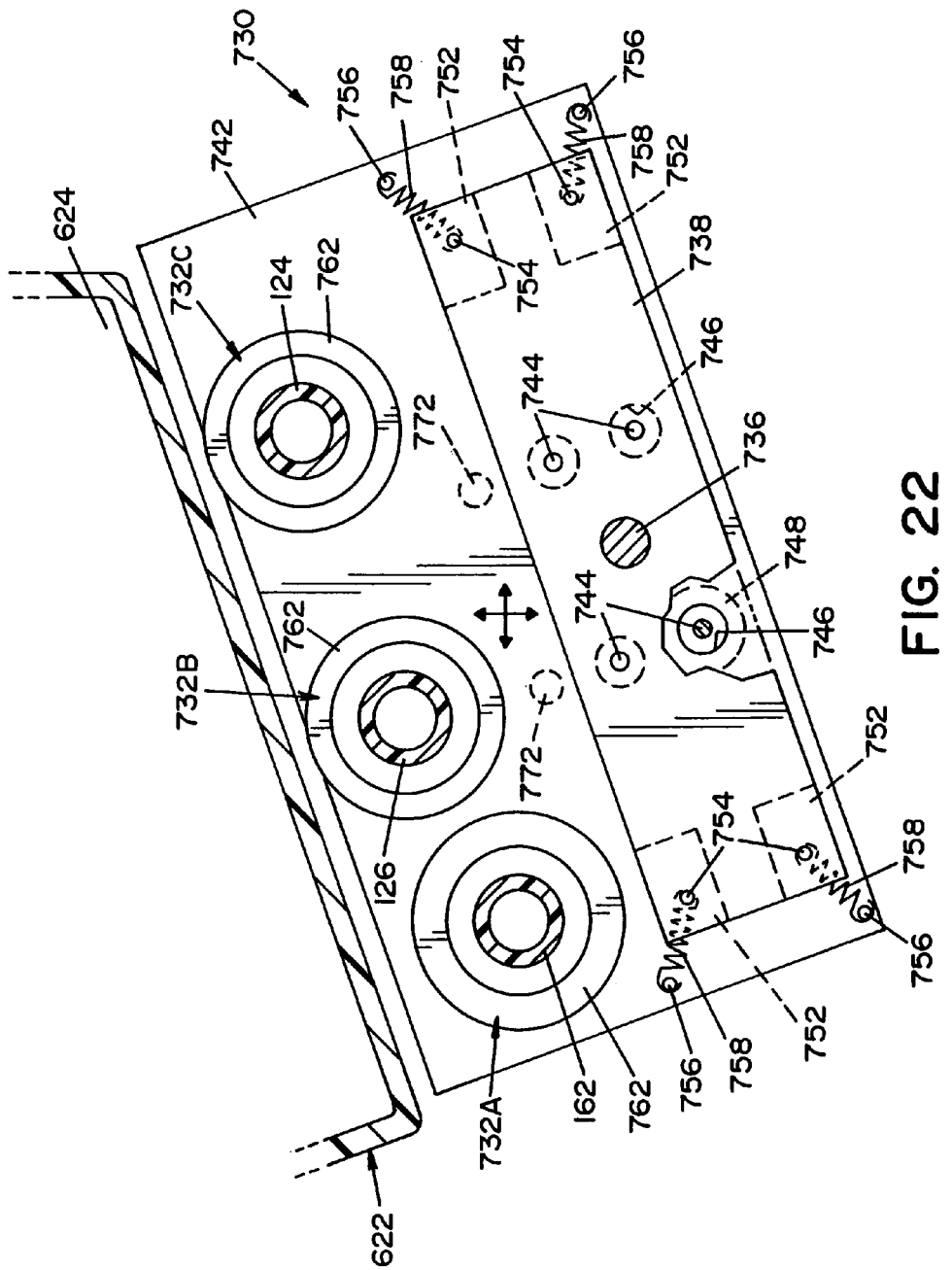
FIG. 22 is a sectional view taken along lines 22-22 of FIG. 19.

Referring now to FIGS. 19, 21, and 22, platen section 730 of connector assembly 660 is best seen. Platen section 730 includes an actuator 734 connected to housing structure 22 for reciprocally moving female connectors 732A, 732B, 732C into and out of engagement with male connectors 672A, 672B, 672C, respectively, on manifold section 670. In the embodiment shown, actuator 734 is a pneumatic cylinder having a rod 736 extending therefrom. The free end of rod 736 is threaded to receive a support bar 738. In the embodiment shown, support bar 738 is generally rectangular in shape and has a flat mounting surface 738a on one side thereof. A larger rectangular plate 742 is mounted to support bar 738. In the embodiment shown, spaced-apart, elongated fasteners 744 extend through apertures 746 in plate 742 into support bar 738 to mount plate 742 to support bar 738. As best seen in FIGS.

21 and 22, plate 742 is significantly larger than support bar 738. Plate 742 is mounted to support bar 738, along one side of plate 742. As best seen in FIG. 22, apertures 746 within plate 742 are significantly larger than the diameter of fasteners 744. In the embodiment shown, fasteners 744 are elongated cap screws. A washer 748 is disposed over enlarged apertures 746. A biasing spring 749 is disposed between the head of each cap screw fasteners 744 and washer 748.

Recesses 752 are formed at the corners of support bar 738 and define cavities between support bar 738 and mounting plate 742, as best seen in FIG. 23. Within each recess 752, a pin 754 is mounted to support bar 738. Each pin 754 on support bar 738 has an associated pin 756 mounted on plate 742, as best seen in FIG. 22. Tension springs 758 are attached to the associated pins 754, 756. In this respect, plate 742 is movable relative to support bar 738 in all three directions. Specifically, plate 742 may slide across surface 738a of support bar 738 within the limits allowed by the dimensions of aperture 748 in plate 742 that surrounds fasteners 744. Tension springs 758 mounted to pins 754, 756 on support bar 738 and plate 742 act as a means for centering plate 742 relative to support bar 738. Similarly, because plate 742 is mounted to support bar 738 along one side of plate 742, plate 742 may rotate slightly relative to support bar 738 if sufficient force is applied to the end of plate 742. As illustrated in FIGS. 21 and 22, support bar 738 and plate 742 are disposed at an angle to accommodate the orientation of drawer tray 622.

Female connectors 732A, 732B, 732C are mounted to the free end of plate 742. Each connector 732A, 732B, 732C has a base portion 762 having a threaded nipple 762a that extends through a hole in plate 742. A threaded collar 764 attaches to nipple 762a to secure base section 762 of each connector 732A, 732B, 732C to plate 742. Female connectors 732A, 732B, 732C are spaced apart to be in registry with male connectors 672A, 672B, 672C, respectively, on manifold section 670. In this respect, actuator 734 is disposed relative to housing structure 22 and relative to manifold block 674, such that reciprocal movement of actuator rod 736 engages or disengages female connectors 732A, 732B, 732C on platen section 730 to male connectors 672A, 672B, 672C on manifold section 670. Base sections 762 of female connectors 732A, 732B, 732C are preferably attached to flexible tubing 766 to allow movement of platen section 730. Female connector 732A is attached to return line 162. Female connector 732B is connected to second branch feeder line 126 of fluid circulation system 100. Female connector 732C is connected to first branch feeder line 124 of fluid circulation system 100.

To assist in aligning female connectors 732A, 732B, 732C on platen section 730 with the male connectors 672A, 672B, 672C on manifold section 670, aligning pins 772 extend from plate 742, as best seen in FIG. 19. Aligning pins 772 are parallel to each other and include rounded leading ends 772a. Pins 772 are disposed to be in alignment with locating openings 724 in manifold block 674. As illustrated in FIG. 19, the positioning of aligning pins 772 into locating openings 724 in manifold block 674 ensures that female connectors 732A, 732B, 732C on platen section 730 align with the male connectors 672A, 672B, 672C on manifold section 670.

Figure 24:
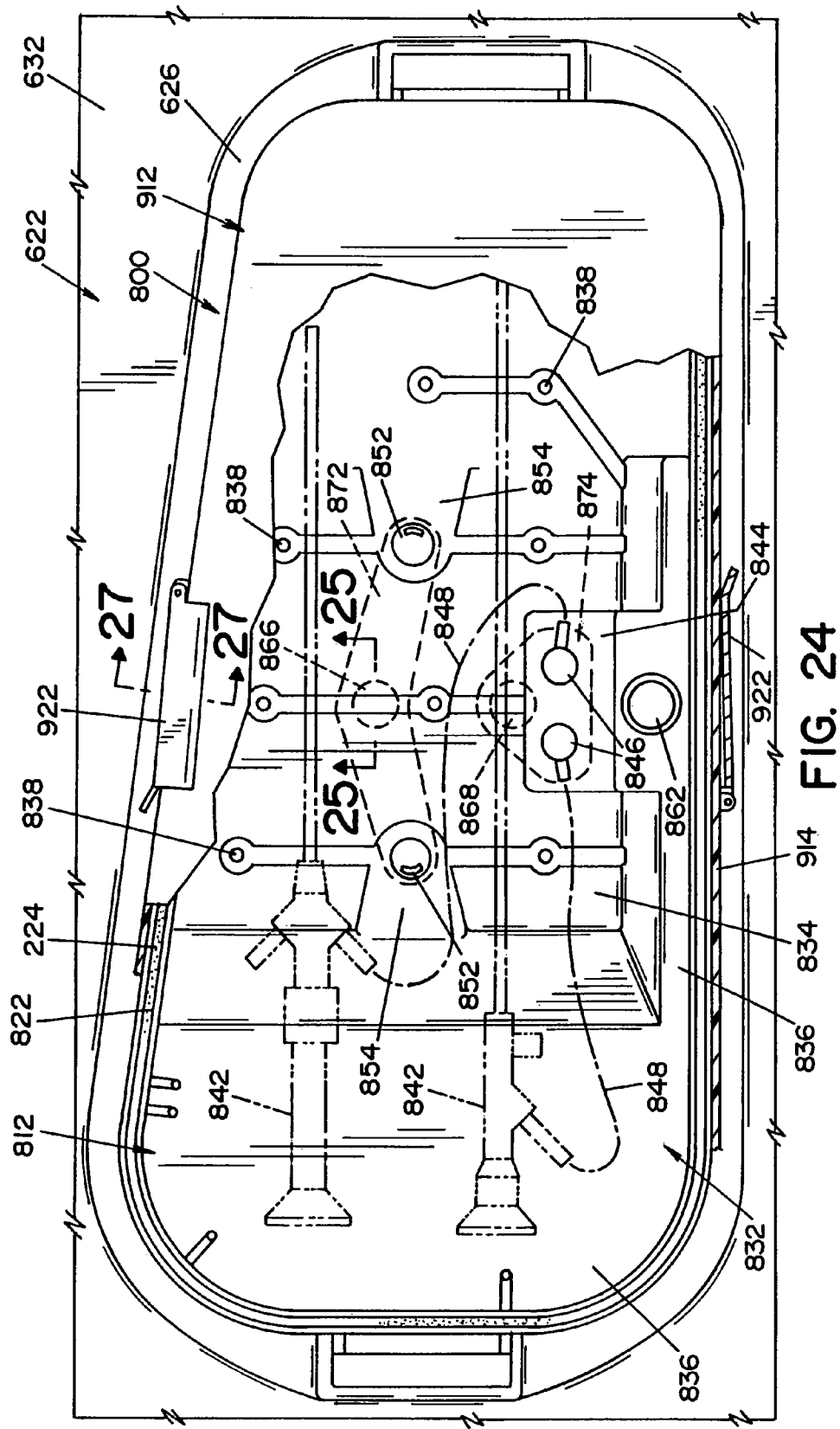
FIG. 24 is a top plan view of an instrument storage container used in the apparatus shown in FIG. 1.

The ability of plate 742 to float, i.e., move to a limited extent in all three directions on support bar 738, helps facilitate proper alignment and engagement between the female connectors 732A, 732B, 732C on movable platen section 730 and male connectors 672A, 672B, 672C on manifold section 670 that is stationary when the drawer tray 622 is in the closed position Container 800 has a shape wherein container 800 can be received in cavity 624 in drawer tray 622 in one orientation, as illustrated in FIG. 24.

Instrument Container 800

Referring now to FIGS. 24-27, instrument container 800 is best seen. Instrument container 800 is generally comprised of tray 812 and lid 912 that is attachable to tray 812. Tray 812 is generally cup-shaped and has a bottom wall 814 and a continuous side wall 816 that extends about the periphery of bottom wall 814 to one side thereof. Bottom wall 814 and side wall 816 define a cavity 818 in which medical instruments or other items to be deactivated are to be inserted.

Figure 27:
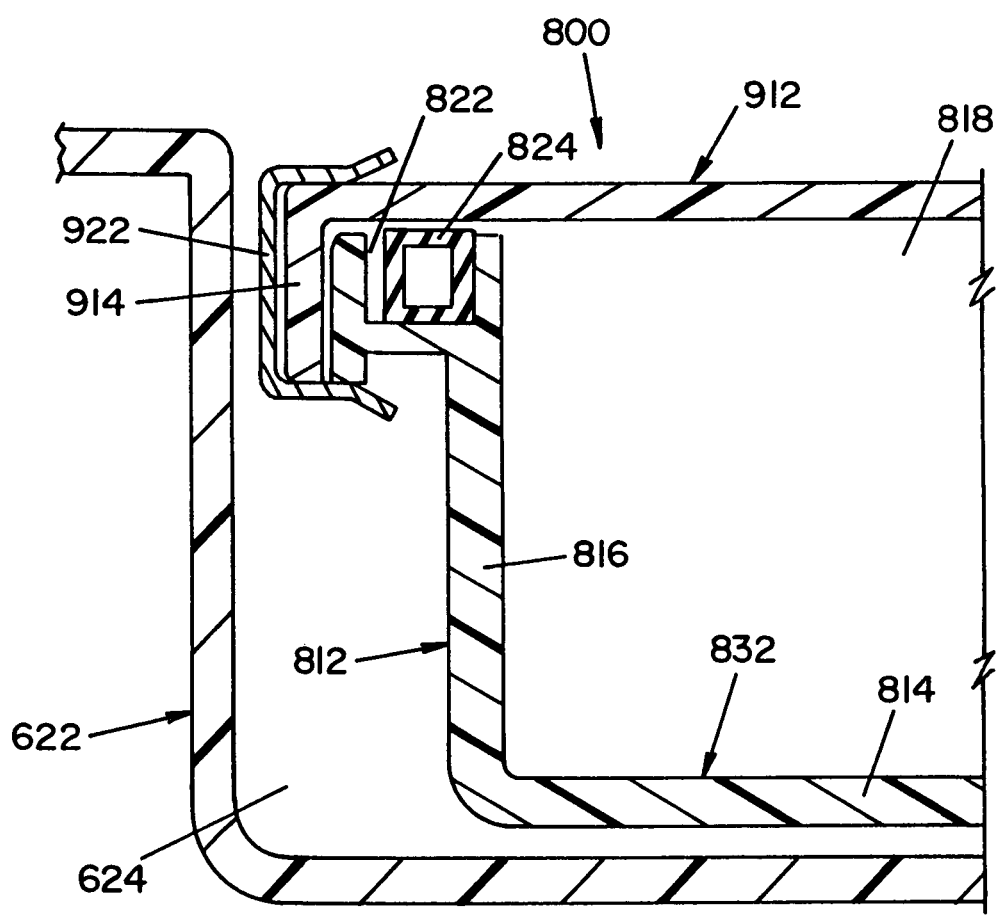
FIG. 27 is a sectional view taken along lines 27-27 of FIG. 24, showing a seal arrangement on the instrument storage container.

The upper edge of side wall 816 is shaped to define a channel 822, best seen in FIG. 27. Channel 822 extends continuously about the upper edge of side wall 816. Channel 822 is dimensioned to receive a continuous, flexible seal 824. In the embodiment shown, seal 824 is an inflatable seal. An air conduit 826, schematically illustrated in FIG. 4, communicates with seal 824 by means of a fitting (not shown) that is mounted to instrument container 800.

Bottom wall 814 is formed to have a contoured upper surface 832. Bottom wall 814 includes a centrally located mounting pad 834 that is surrounded by a trough 836. Mounting pad 834 is generally rectangular in shape and includes a number of upwardly extending, spaced-apart pins or posts 838. Pins or posts 838 are provided to receive and support (shown in phantom in FIG. 24) medical instruments 842 or items to be microbially decontaminated. Mounting pad 834 has a recess or relief 844 formed therein. Recess or relief 844 is formed along the edge of mounting pad 834 and has an upper surface that is disposed above trough 836. Connection fittings 846 are disposed within recess or relief 844. Two directional spray nozzles 852 are mounted onto mounting pad 834. Spray nozzles 852 are dimensioned to generate fan-like spray patterns that are directed to the longitudinal ends of tray 812. Spray nozzles 852 are disposed in shallow fan-like recesses 854 formed in the mounting pad 834.

A drain fluid assembly 862 is formed in bottom wall 814 of tray 812 to allow a microbial deactivation fluid to flow out of instrument container 800. Drain fluid assembly 862 is disposed within trough portion 836 adjacent to side wall 816 and shall be dimensioned as described below.

In the embodiment shown, two inlet fluid assemblies 866, 868 are formed in tray 812 to allow a microbial deactivation fluid to flow into instrument container 800. Fluid inlet assembly 866 facilitates flow of a microbial deactivation fluid into tray 812 through spray nozzles 852. Fluid inlet assembly 866 communicates with a V-shaped, internal cavity 872, formed within bottom wall 814 of tray 812, as illustrated by dashed lines in FIG. 24. Cavity 872 communicates with spray nozzles 852. Fluid inlet assembly 868 facilitates fluid flow to connection fittings 846 within relief or recess 844 in mounting pad 834. Connection fittings 846 are connectable to certain medical devices and instruments by flexible connectors 848 (depicted by phantom lines in FIG. 24) to direct a microbial deactivation fluid through lumens or passages within instruments 842. Fluid inlet assembly 868 communicates with a generally triangular-shaped cavity 874 formed within bottom wall 814 of tray 812. Cavity 874 communicates with connecting fitting 846.

Figure 25:
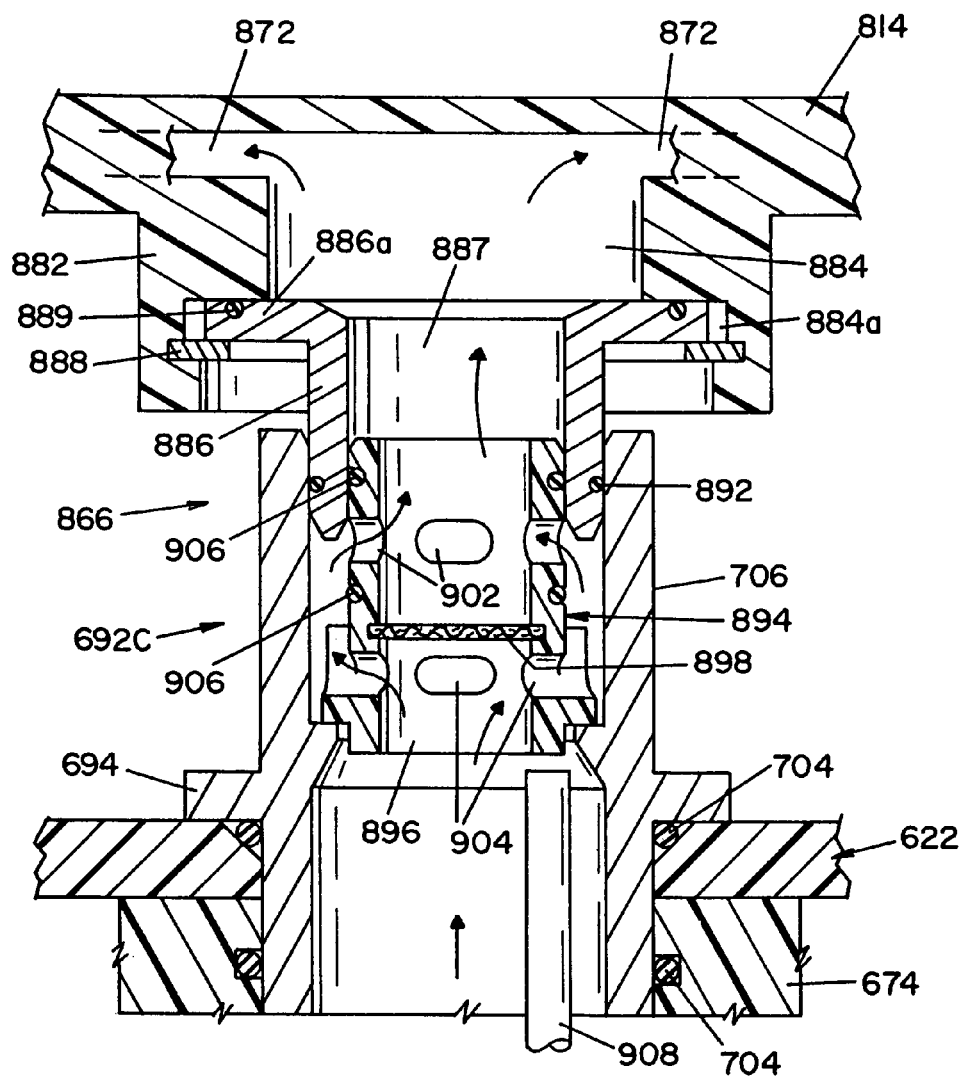
FIG. 25 is a sectional view taken along lines 25-25 of FIG. 24, showing a valve assembly in an opened position.

Fluid inlet assemblies 866, 868 and drain fluid assembly 862 are essentially identical and, therefore, only fluid inlet assembly 866 shall be described in detail. Another embodiment of fluid inlet assembly 866 is shown in FIG. 25. Fluid inlet assembly 866 is disposed within a cylindrical boss 882 that is formed on the underside of bottom wall 814 of tray 812. An opening 884 of varying diameter extends into boss 882 and communicates with v-shaped cavity 872. A sleeve 886 having an outward-extending flange 886a is disposed within opening 884, such that sleeve 886 extends downward, out from boss 882. Sleeve 886 defines an inner cylindrical passage 887. A retaining ring 888 within a slot in boss 882 secures sleeve 886 in boss 882. An o-ring 889 is disposed between flange 886a of sleeve 886 and boss 882 to form a fluid-tight seal therebetween.

Opening 884 has a section 884a dimensioned to receive outward extending flange 886a. In this respect, flange 886a of sleeve 886 is retained within opening 884 by a retaining ring 888. Section 884a of opening 884 and flange 886a of sleeve 886 are dimensioned such that flange 886a is retained wherein sleeve 886 can move, i.e. float, from side to side. The extent of lateral, or side to side movement of sleeve 886 is limited by contact between the edge of extending flange 886a and surface 884a of opening 884.

Sleeve 886 has an outer diameter dimensioned to be received within collar 706 of connector insert 692C on drawer tray 622. An o-ring 892 is disposed in the outer surface of sleeve 886 to form a fluid-tight connection therewith. It can be appreciated that the floating movement of sleeve 886 within opening 884 provides for alignment of sleeve 886 with collar 706.

A valve element 894 is disposed within passage 887 in sleeve 886. Valve element 894 is tubular in shape and has an opening 896 extending axially therethrough. A barrier 898 is disposed within opening 896. Barrier 898 is comprised of a filter material that is gas and vapor permeable, i.e., is capable of allowing moisture and gas to pass therethrough but prevents liquid, bacteria, and/or organisms from passing therethrough. A first set of spaced-apart apertures 902 are formed in the side of valve element 894 to one side of barrier 898. A second set of spaced-apart apertures 904 are formed in the side of valve element 894 to the other side of barrier 898. O-rings 906 are provided on the external surface of valve element 894 to form a fluid-tight seal with the inner surface of sleeve 886.

Figure 26:
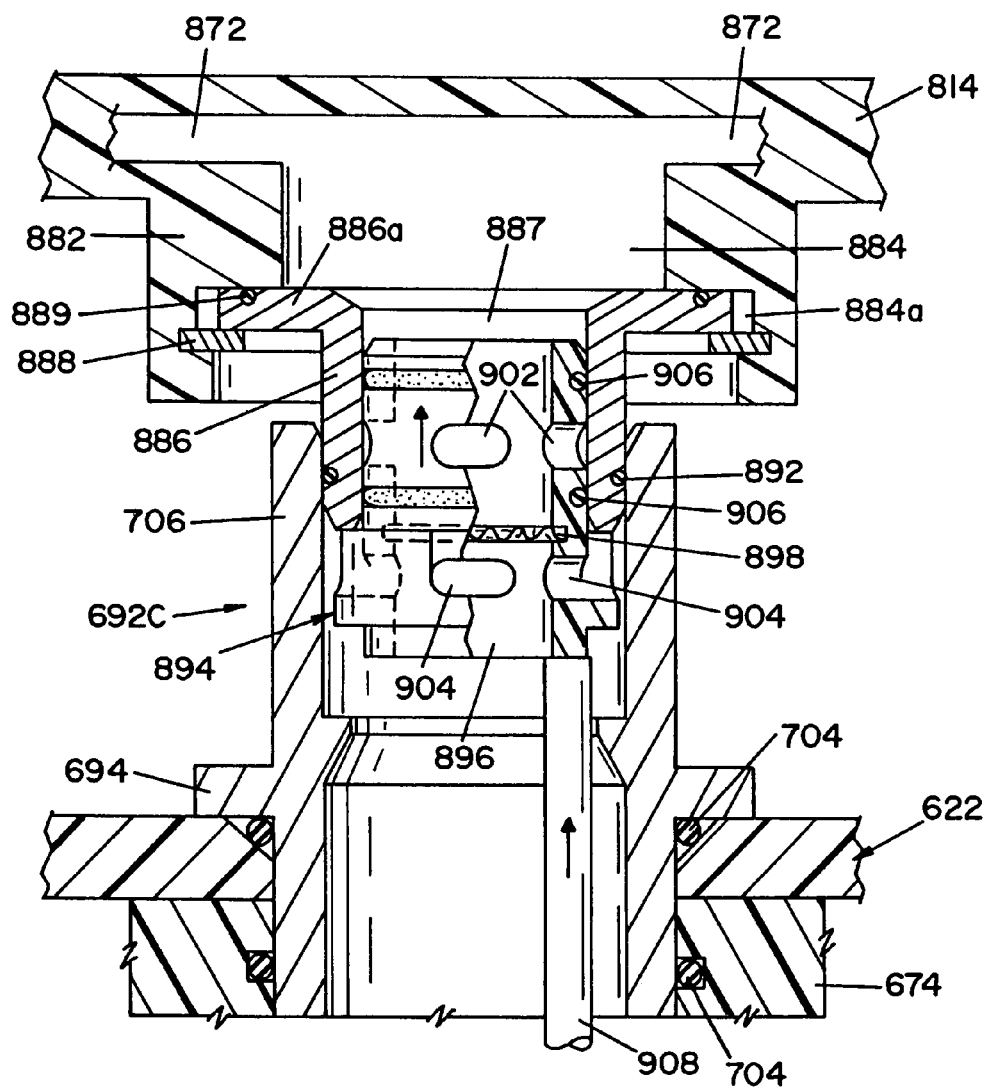
FIG. 26 is a sectional view of the valve assembly shown in FIG. 25, showing the valve assembly in a closed position.

Valve element 894 is movable between an open position, shown in FIG. 25, and a closed position, shown in FIG. 26. In the open position, fluid may flow around barrier 898 into instrument container 800, as depicted by the arrows in FIG. 25. In the closed position, valve element 894 is moved up into sleeve 886, wherein apertures 902 are within sleeve 886 and barrier 898 prevents liquids, bacteria, and/or organisms from passing into container 800.

Valve element 894 is in an open position during a decontamination cycle. Following a decontamination cycle and before container 800 can be removed from drawer tray 622, an actuator 908, schematically illustrated as a pin in FIGS. 25 and 26, moves valve element 894 from an open position to a closed position.

Referring now to FIGS. 29A through 29D, a fluid inlet assembly 1200 illustrating another embodiment of the present invention is shown. Fluid inlet assembly 1200 is basically comprised of container connector assembly 1210 and a valve element 1240. Fluid inlet assembly 1200 is dimensioned to operatively mate with a tray post 1310. Container connector assembly 1210 is comprised of a cylindrical boss 1212 and a sleeve 1214. In the embodiment shown, cylindrical boss 1212 is formed on the underside of bottom wall 814 of tray 812. Cylindrical boss 1212 has an inner surface 1216 of various diameters that define an opening 1218 extending through cylindrical boss 1212. Opening 1218 is in fluid communication with v-shaped cavity 872. Surface 1216 includes a downward-facing annular surface 1216a. Surface 1216 defines annular slot 1223 adjacent, i.e. below, annular surface 1216a.

Figure 29A:
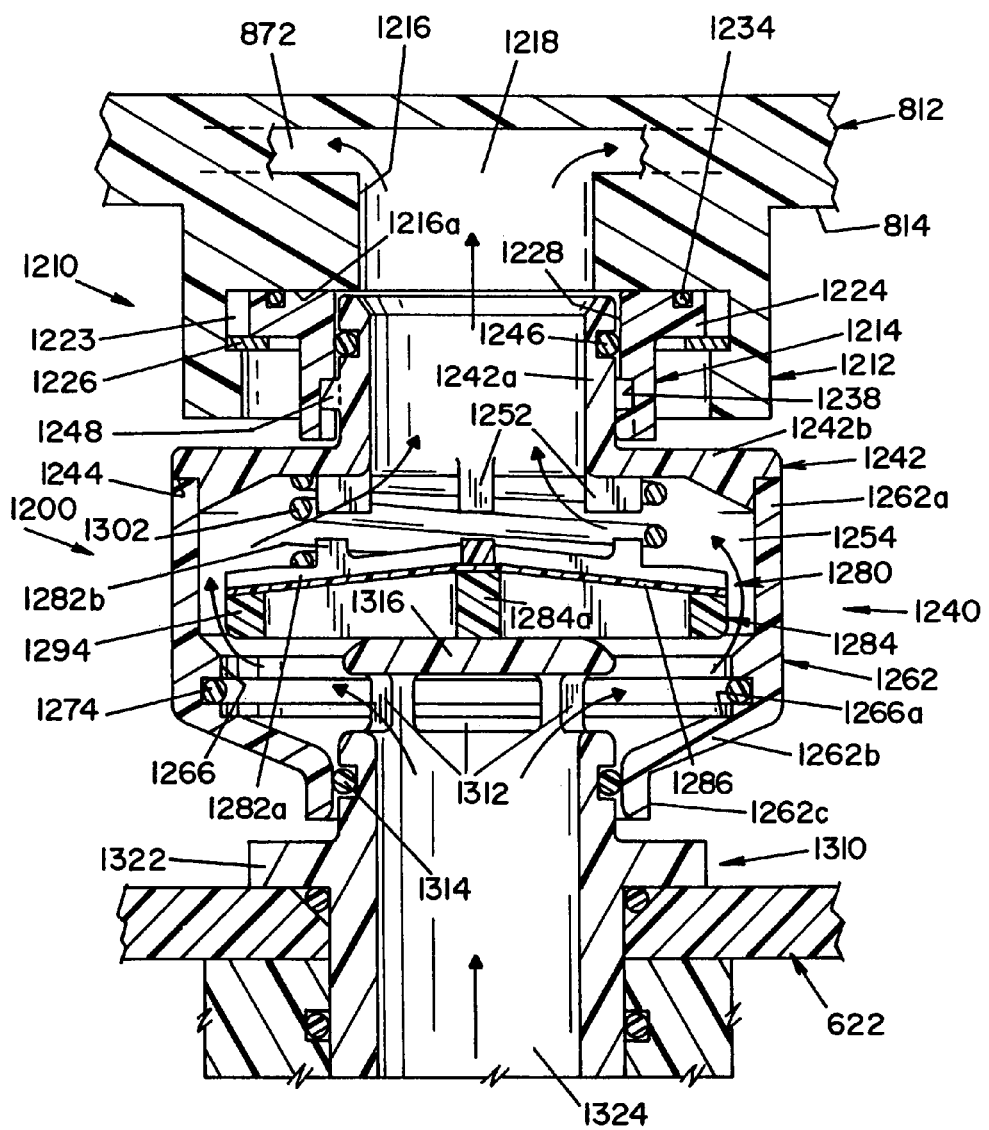
FIG. 29A is a sectional view of an alternate embodiment of a valve assembly, showing the valve assembly in a first position.

Sleeve 1214 is cylindrical in shape and has an outward extending flange 1224 formed at one end of sleeve 1214. A grove is formed in the upper surface of outward extending flange 1224. The grove is dimensioned to accept an o-ring 1234. O-ring 1234 extends around the upper opening in sleeve 1214, as shown in FIG. 29A. Sleeve 1214 defines an inner cylindrical passage 1228. Formed in the inner wall of sleeve 1214 is a locking grove 1238.

As shown in FIG. 29A, sleeve 1214 is dimensioned to be disposed within opening 1218 of cylindrical boss 1212. A retaining ring 1226 and outward extending flange 1224 are dimensioned to be located in annular slot 1223. Retaining ring 1226 and outward extending flange 1224 are dimensioned such that o-ring 1234 on outward extending flange 1224 creates a fluid-tight seal with downward-facing annular surface 1216a of cylindrical boss 1212. The outer diameter of outward extending flange 1224 is smaller than the diameter of annular slot 1223 such that sleeve 1214 can move, i.e. float, from side to side. The later movement of sleeve 1214 is limited by contact with annular slot 1223. Cylindrical passage 1228 of sleeve 1214 provides fluid communication with opening 1218 of cylindrical boss 1212.

Figure 29B:
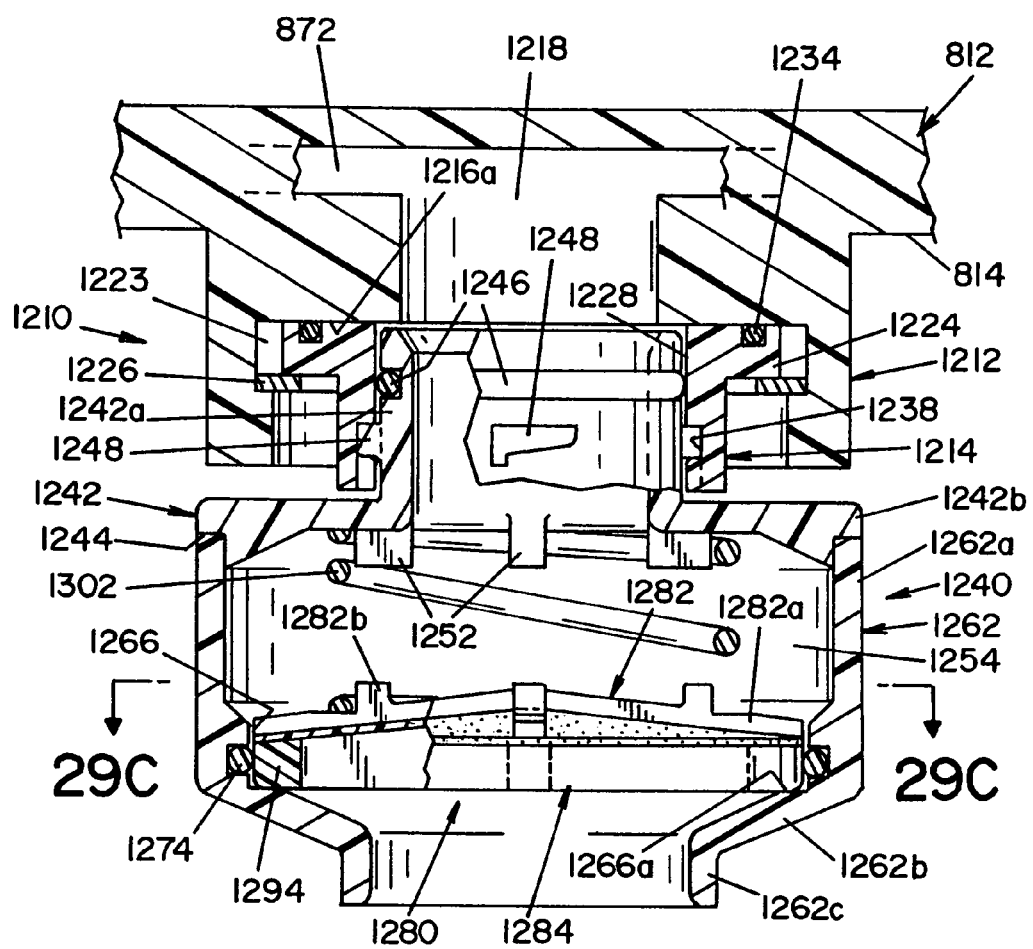
FIG. 29B is a partially sectioned view of the valve assembly of FIG. 29A, showing the valve assembly in a second position.

Valve element 1240 is composed of an upper housing 1242 and a lower housing 1262. Upper housing 1242 and lower housing 1262 are dimensioned to be joined together to define an inner cavity 1254. Upper housing 1242 has a tubular section 1242a and a flange section 1242b extending from the bottom of tubular section 1242a. A locking tab 1248 is located on the outer surface of tubular section 1242a. The outer surface of tubular section 1242a has an annular grove located above locking tab 1248. The grove is dimensioned to accept an o-ring 1246 that extends around tubular section 1242a as shown in FIG. 29B. A series of tabs 1252 are located on the bottom side of flange section 1242b. Tabs 1252 extend downward from flange section 1242b and are located around the opening through upper housing 1242. An annular shoulder 1244 is defined along the bottom surface of flange section 1242b. Shoulder 1244 extends around the outer perimeter of flange section 1242b.

Lower housing 1262 is tubular in shape with a cylindrical upper portion 1262a and a conical lower section 1262b that tapers down to a cylindrical collar portion 1262c. Lower housing 1262 defines a cavity. The cavity includes a bored opening 1266 formed in cylindrical upper portion 1262a. An annular seat 1266a is defined in the lower end of the bored opening 1266. An annular grove is formed in the bored opening 1266 above the annular seat 1266a. The grove is dimensioned to accept an o-ring 1274. The inner surface of conical lower section 1262b is formed to define a conical surface that leads into bored opening 1266.

Shoulder 1244 in upper housing 1242 is dimensioned to receive the upper edge of cylindrical upper portion 1262a of lower housing 1262. Upper housing 1242 and lower housing 1262 are preferable formed from a plastic material, and permanently attached to each other using sonic welding, spin welding or an adhesive. Upper housing 1242 and lower housing 1262 define an inner cavity 1254. A filter element 1280 and a spring element 1302 are disposed in cavity 1254.

Figure 29C:
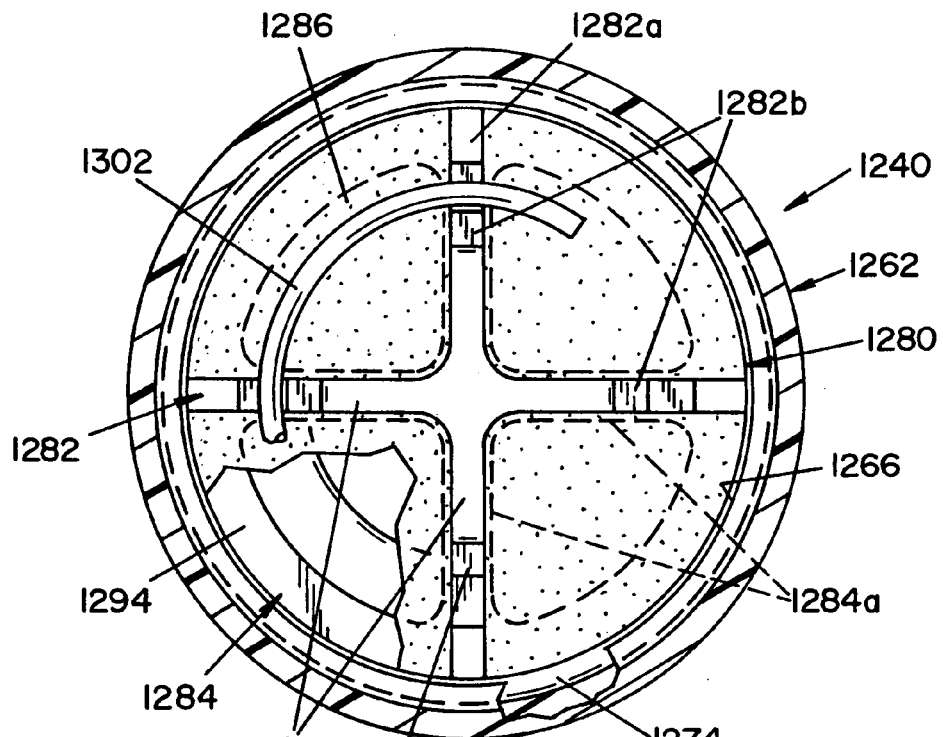
FIG. 29C is partially section view taken along lines 29C-29C of FIG. 29B, showing a filter element.
Figure 29D:
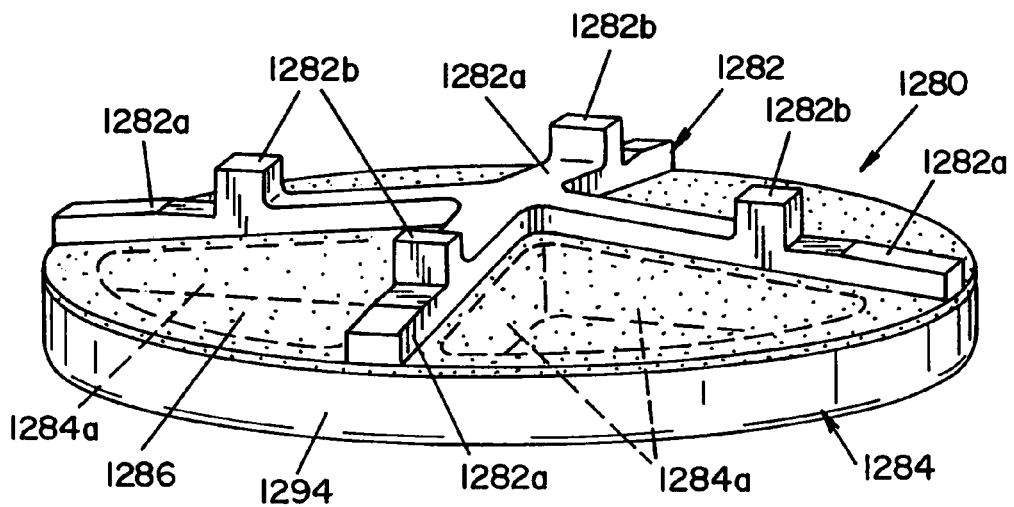
FIG. 29D is a perspective view of the filter element.

Referring now to FIGS. 29C and 29D, filter element 1280 is best seen. Filter element 1280 is comprised of an upper filter support 1282, a lower filter support 1284 and a filter membrane 1286. Upper filter support 1282 is comprised of a plurality of equally spaced-apart, outwardly-extending rib sections 1282*a* that are connected at one end. Each rib section 1282*a* has a tab 1282*b* located on the upper surface of each rib section 1282*a*.

Lower filter support 1284 is comprised of a plurality of radially extending rib sections 1284*a* that are joined together at one end and connected to a ring 1294 at another end. Rib sections 1282*a* in upper filter support 1282 are dimensioned to overlay rib sections 1284*a* in lower filter support 1284 to exposed a filter membrane 1286, as best seen in FIG. 29C.

Filter membrane 1286 is comprised of a filter material that is permeable to gas and vapor, i.e., is capable of allowing moisture and gas to pass therethrough but impermeable to liquid, bacteria, and/or organisms from passing therethrough. Suitable filter medium material includes by way of example and not limitation, PVDF, or PTFE (polytetraflouroethylene). Filter membrane 1286 is generally circular in shape and is dimensioned to be located between upper filter support 1282 and lower filter support 1284.

Upper filter support 1282, lower filter support 1284 and filter membrane 1286 are attached to each other in a manner to capture filter membrane 1286 between upper filter support 1282 and lower filter support 1284. Upper filter support 1282, lower filter support 1284 and filter membrane 1286 may be attached using sonic welding or adhesive to create a filter element 1280.

Filter element 1280 is dimensioned to be disposed within cavity 1254. Filter element 1280 is further dimensioned to be accepted into bored opening 1266 and rest on annular seat 1266*a*. Ring 1294 of filter element 1280 is dimensioned to sealingly engage o-ring 1274 to form a fluid tight seal between filter element 1280 and lower valve housing 1262, as shown in FIG. 29B.

Spring element 1302 is located above filter element 1280 to bias filter element 1280 to a first position as shown in FIG. 29B. The inner diameter of spring element 1302 is dimensioned to fit around tabs 1252 in upper housing 1242 and tabs 1282*b* on filter element 1280.

As shown in FIG. 29B, valve element 1240 is dimensioned to be received into sleeve 1214. In this respect, the outer diameter of tubular section 1242*a*, o-ring 1246 and inner diameter of sleeve 1214 are dimensioned to create a fluid-tight seal between sleeve 1214 and valve element 1240. Valve element 1240 may be secured to sleeve 1214 in a twist-lock or threaded fashion to engage locking tab 1248 of valve element 1240 into locking grove 1238 of sleeve 1214.

Tray post 1310 is generally tubular in shape with one closed end 1316 and a flange 1322 extending from the side wall of post 1310. The inner wall of post 1310 defines an inner cavity 1324. Located below closed end 1316 is a series of apertures 1312 that allow fluid communication to inner cavity 1324. Located below apertures 1312 is a grove that is dimensioned to accept an o-ring 1314 that extends around the tubular portion of tray post 1310. The diameter of the portion of post 1310 below flange 1322 is dimensioned to be accepted into drawer tray 622.

As shown in FIG. 29A, tray post 1310 is dimensioned to be accepted into the cylindrical collar portion 1262*c* of valve element 1240 when container 800 is placed into drawer tray 622. O-ring 1314 creates a fluid tight first seal between tray post 1310 and valve element 1240 when tray post 1310 is received into cylindrical collar portion 1262*c* of valve element 1240. As container 800 is being placed into drawer tray 622, tray post 1310 engages valve element 1240. Engagement of tray post 1310 with valve element 1240 causes tray post 1310 to contact lower filter support 1284 to move filter element 1280 to a second position, best seen in FIG. 29A. In this second position, cavity 1324 in tray post 1310, cavity 1254 in valve element 1240 and opening 1218 in cylindrical boss 1212 are all in fluid communication. When filter element 1280 is in the second position, fluid can flow around filter element 1280 as shown by the arrows in FIG. 29A.

Filter element 1280 is in a second position, as shown in FIG. 29A, during a decontamination cycle. Following a decontamination cycle container 800 is removed from drawer tray 622. As container 800 is removed from tray 622, tray post 1310 is also withdrawn from valve element 1240. As tray post 1310 is being removed from valve element 1240, spring element 1302 forces filter element 1280 down into bored opening 1266. Before tray post 1310 is completely withdrawn from valve element 1240, filter element 1280 sealing engages o-ring 1274 to create a fluid-tight seal between filter element 1280 and lower valve housing 1262. Valve element 1240 is designed such that the seal between filter element 1280 and lower valve housing 1262 is reestablished before the seal between tray post 1310 and valve element 1240 is broken. As tray post 1310 continues to be withdrawn from valve element 1240, the seal between tray post 1310 and valve element 1240 is broken. In this respect, valve element 1240 is designed to create a microbial barrier between the medical instruments and devices in container 800 and the environment before container 800 is completely removed from drawer tray 622; thereby keeping the medical instruments and devices in container 800 in a microbially deactivated state.

Referring now to FIGS. 24 and 27, lid 912 is best seen. Lid 912 is generally a flat, planar element that is shaped to cover and enclose the opened, upper end of tray 812. Lid 912 includes a downward-extending flange 914 that extends about the periphery of lid 912 and is dimensioned to capture the upper edge of side wall 816, as shown in FIG. 27.

A locking device 922 is provided to secure lid 912 to tray 812. In the embodiment shown, locking device 922 is an elongated, channel-like element that is pinned at one end to tray 812. The channel defined in the locking device 922 is dimensioned to capture the upper edge of tray 812 and lid 912, as shown in FIG. 27.

Storage Cabinet 1000

Figure 28:
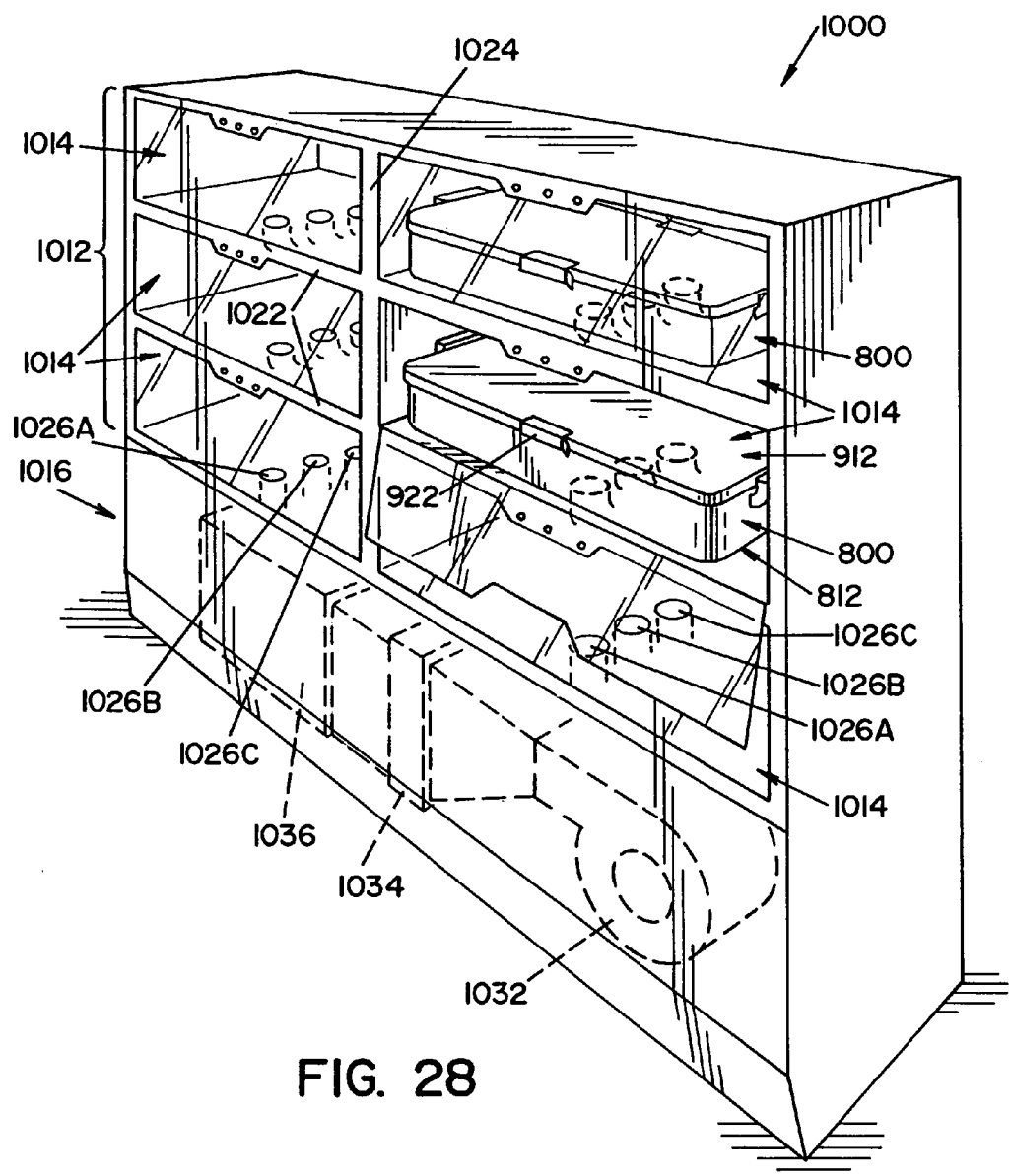
FIG. 28 is a perspective view of a storage cabinet for storing decontaminated instrument containers, illustrating another aspect of the present invention.

Referring now to FIG. 28, a storage cabinet 1000 for storing previously sterilized instrument containers 800 is shown. Storage cabinet 1000 is generally rectangular in shape and includes an upper section 1012 having a plurality of storage compartments 1014 and a lower enclosed section 1016. Upper section 1012 includes a plurality of horizontal shelves 1022 and a central vertical divider 1024 that divides shelves 1022 into side-by-side compartments 1014. Compartments 1014 are dimensioned to receive instrument storage containers 800. Each shelf 1022 includes three female connectors 1026A, 1026B, 1026C that are dimensioned to mate with connectors (not shown) on the bottom of tray 812 of instrument container 800. In this respect, female connectors 1026A, 1026B, 1026C are generally similar to the connectors in drawer tray 622 of drawer assembly 600. Drain opening 862 and sleeves 886 of fluid inlet assemblies 866, 868 on the bottom of instrument container 800 align and mate with female connectors 1026A, 1026B, 1026C on cabinet shelves 1022. With respect to an alternative embodiment of the invention, valve elements 1240 are located on the bottom of instrument container 800. In this embodiment, connectors 1026A, 1026B and 1026C are similar to tray posts 1310 and are dimensioned to mate to valve elements 1240 (not shown) on the bottom of tray 812 of instrument container 800.

A blower 1032 is provided in the enclosed lower section 1016 of storage cabinet 1000. The outlet end of blower 1032 is connected to female connectors 1026B, 1026C on shelves 1022 of storage cabinet 1000 by internal ducts and conduits (not shown). A filter 1034 is disposed downstream of blower 1032 to filter the air being blown to the ducts to female connectors 1026B, 1026C. A heater 1036 is provided downstream of filter 1034 to heat the air blown to instrument container 800. Female connectors 1026B, 1026C connect to the inlet ports of container 800. Connector 1026A on shelves 1022 connects to the drain port of instrument container 800. Storage cabinet 1000 is operable to blow filtered, warm air through instrument containers 800 and through the instruments contained therein to dry the medical instruments and the interior of container 800 following a decontamination cycle.

Control means (not shown) can selectively direct the dry filtered air to specific containers 800 within storage cabinet 1000. Barrier elements 898 in fluid inlet assemblies 866, 868 and drain fluid assembly 862, as heretofore described, in instrument container 800 allow moisture and air to flow in and out of containers 800 but prevent organisms and bacteria from entering container 800.

Storage cabinet 1000 thus provides a method of storing medical instruments in a decontaminated state, awaiting further use.

Operation of System

Apparatus 10 shall now further be described with reference to the operation thereof. One or more items to be deactivated, such as medical, dental, pharmaceutical, veterinary or mortuary instruments or the devices, are loaded into the instrument container 800. Instrument container 800 can accommodate numerous types of medical instruments and items. Certain medical instruments, such as bronchoscopes and endoscopes, have lumens, i.e., passages, extending therethrough. Flexible connectors 848 (not shown in detail) are used to connect fluid passages 874 in tray 812 to the internal lumens of the medical instruments. More specifically, flexible connectors 848 are dimensioned to attach to connection fittings 846 within tray 812 and to attach to the fittings on the medical instruments, so as to enable microbial deactivation fluid to be forced through the lumens of the medical instruments. Once flexible connectors 848 have been attached to tray 812 and the medical instrument, lid 912 is placed over tray 812 and is locked into position, using latch element 922 on tray 812.

With the instruments or items to be microbially decontaminated positioned within instrument container 800, an operator opens drawer assembly 600 of apparatus 10 to allow instrument container 800 to be placed within drawer tray 622.

A decontamination cycle for apparatus 10 includes a number of specific phases that shall now be described.

Preparation Phase

During a user-preparation phase, drawer assembly 600 of apparatus 10 is movable between a closed position shown in FIG. 1 and an open position shown in FIG. 2 by manual manipulation of control button 636 on front panel 634. A valve element 894 is place into each connector inserts 692C, 692B, 692C, as shown in FIG. 25, if the devices to be decontaminated will be stored at the end of the decontamination cycle. Similarly, in an alternate embodiment, valve element 1240 is secured to sleeve 1214 by engaging locking tab 1248 on valve element 1240 into locking grove 1238 in sleeve 1214 for each container connector assembly 1210 on container 800. In preparation for a decontamination cycle, instrument container 800 with the instruments or items to be deactivated is placed within drawer tray 622 in drawer assembly 600. As illustrated in the drawings, cavity 624 in tray 622 and the shape of instrument container 800 are such that instrument container 800 may be placed within cavity 624 in only one orientation. This ensures that drain fluid assembly 862 and fluid inlet assemblies 866, 868 on instrument container 800 align with the corresponding drain and connector inserts 692A, 692B, 692C within drawer tray 622.

With instrument container 800 placed within drawer tray 622, drawer assembly 600 is moved to a closed position, using drawer control button 636.

During this user-preparation phase, a chemistry-holding device 430 is inserted within the chemistry-delivery system 400. To this end, access panel 22a on housing structure 22 is moved to an open position to expose lid 520 of chemistry-delivery system 400. Lid 520 is unlatched and opened to expose compartments 482, 484 in chemistry-delivery system 400. Chemistry-holding device 430 is removed from package 412 by peeling away cover 416 of chemistry-storage package 412. Chemistry-holding device 430 is inserted within housing 470 with polymer layer 462 over compartment 484 beneath blade 582 on lid 520. Lid 520 is closed and latched, as illustrated in FIG. 17. In this position, blade 582 on lid 520 punctures polymer layer 462 covering compartment 484.

System-Sealing Phase

With instrument container 800 within drawer tray 622 of drawer assembly 600 and drawer assembly 600 in a closed position, a decontamination cycle may be initiated. A first phase of the decontamination cycle is a system-sealing phase, wherein air is applied to inflatable bladder 646 above plate 642. Inflating bladder 646 forces static seal 644 on plate 642 down into engagement with the planar surface of drawer tray 622, thereby forming a complete seal around cavity 624 in drawer tray 622, and forming a sealed, decontamination chamber containing instrument container 800. Inflating bladder 646 is maintained throughout the decontamination cycle.

Fill Phase

With bladder 646 sealing instrument container 800 within the decontamination chamber, a fill phase is initiated. Valves 147, 168, 198, 274 and 327 in drain lines 146, 166, 196, 272 and 328, respectively, are in a closed position. Also closed are valves 164, 236, 246, 284, 286 and valves 254, 276 to the chemistry-delivery system 400. Valve 125 is in a first position as described above. The remaining valves throughout apparatus 10 are opened to allow water from inlet line 102 to enter system feed line 122 and flow throughout fluid circulation system 100. Incoming water is first filtered by filter elements 106, 108 that remove macro particles above a certain size, such as 0.1 micron or above. Filter elements 106, 108 are sized to successively filter out smaller-sized particles. Incoming water is then treated by UV treatment device 114 that applies ultra-violet (UV) radiation to the water to reduce levels of viruses therein. The incoming water then passes through valve 116 and enters fluid-circulation system 100. Valves 214 and 216 in drain line 212 are in an open position to allow any air trapped in filter element 300 to flow out drain line 212. After a predetermined amount of time, valves 214 and 216 in drain line 212 are then changed from an open position to a closed position. The incoming water is then filtered by filter element 300 within system feeder line 122. Upon exiting filter element 300, 75 to 100% of the flow passes along branch feeder line 124 and flows through heater 132 and valve 125 and then proceeds to fill fluid-circulation system 100, the deactivation chamber, and instrument container 800. Initially valve 158 is an open position to allow any air in the lumens of the medical instruments and other devices to exit into the instrument container 800. After a predetermined amount of time valve 158 is changed from an open position to a closed position.

The incoming water is under pressure from an external source and forces water in fluid-circulation system 100, the deactivation chamber, and instrument container 800. As a result of water entering the apparatus 10, air within the system will migrate toward overflow line 292 that is preferably disposed at the highest point of apparatus 10. Directional check valve 293 allows air and water to exit the decontamination chamber. The presence of water flowing through overflow line 292 is sensed by sensor 294. Water flowing through drain line 292 is indicative that apparatus 10 is filled. The system controller then causes valves 104 and 116 to close, thereby stopping the flow of water into apparatus 10. The foregoing description basically describes the fill phase of a decontamination cycle.

Circulation Phase

Once apparatus 10 is filled with water, the system controller initiates a circulation phase to circulate water throughout fluid-circulation system 100. During the circulation phase, valves 254 and 276 to chemistry-delivery system 400 remain closed and valve 125 remains open to allow heated fluid from branch feeder line 124 to flow into fluid circulation system 100, the deactivation chamber, and instrument container 800. Pumps 172 and 182 are energized to circulate water throughout fluid-circulation system 100, including the deactivation chamber and instrument container 800.

Figure 6:
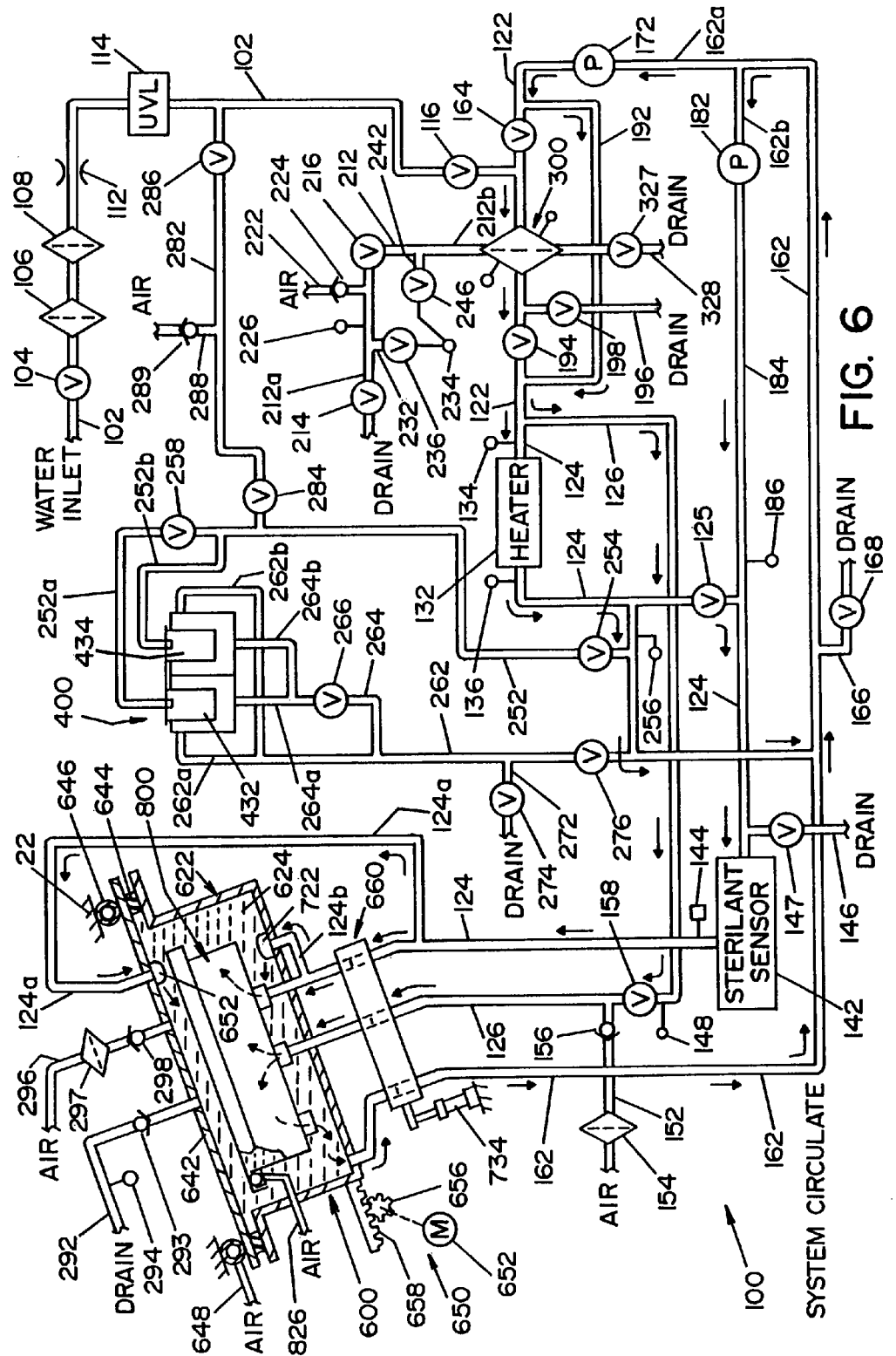
FIG. 6 is a schematic diagram of the reprocessor, illustrating the path of fluids through the reprocessor during a system circulate phase.

FIG. 6 schematically illustrates the flow of fluid throughout fluid-circulation system 100 during the circulation phase. The purpose of the circulation phase is to achieve the proper fluid temperature to deactivate the medical devices in the instrument container. At periods throughout the fill phase and the circulation phase, heater 132 may be activated to increase the temperature of the water flowing through the heater to achieve a desired fluid temperature in the system. Once the desired fluid temperature is achieved, the circulation phase ends.

Chemistry-Generation Phase

Following the circulation phase, valves 254 and 276 to chemistry-delivery system 400 are opened to allow the flow of water therethrough. Initially, valve 258 within section 252*a* of the chemistry-inlet line 252 is closed such that water initially flows into section 252*b* of chemistry-inlet line 252, wherein the water is directed into housing 470 of chemistry-delivery system 400 and, more specifically, into compartment 484 containing the builder components. More specifically, water flows into second inlet passage 496 within housing 470 and up through opening 564 and passage 562 in seal element 542 into cavity 554 defined in seal element 542. As best illustrated in FIG. 17, water flows through apertures 578 in plate 544 into the builders to dissolve the same. The builder components within container 434 of chemistry-holding device 430 dissolve in the water and flow throughout the fluid-circulation system 100. Valve 266 in drain line 264 is closed, thereby preventing the deactivation fluid from draining through drain opening 508 through the bottom of compartment 484. Accordingly, fluid will fill compartment 484 and flow out of compartment 484 through overflow passage 262*b* into section 264*b* of outlet line 262. In this respect, compartment 484 will be filled with fluid up to outlet line 262*b*. Chemistry-housing outlet line 262*b* connects to chemistry-outlet line 262 that, in turn, connects to return line 162, wherein the dissolved builders enter the re-circulation system to be pumped throughout fluid-circulation system 100. The dissolution of builder components creates an alkaline fluid having a predetermined pH level. In one embodiment, the pH level is between about 8.0 and about 9.0. In accordance with one embodiment of the present invention, by flowing water at a known flow rate through compartment 484 containing builder components, an alkaline fluid with a predetermined pH level is created at a predetermined time. The predetermined time is programmed into the system controller. The predetermined time is sufficient to generate an alkaline fluid having a predetermined pH level during each decontamination cycle. It is also contemplated that a sensor may be used to determine when an alkaline fluid having a predetermined ph level has been produced.

Figure 7:
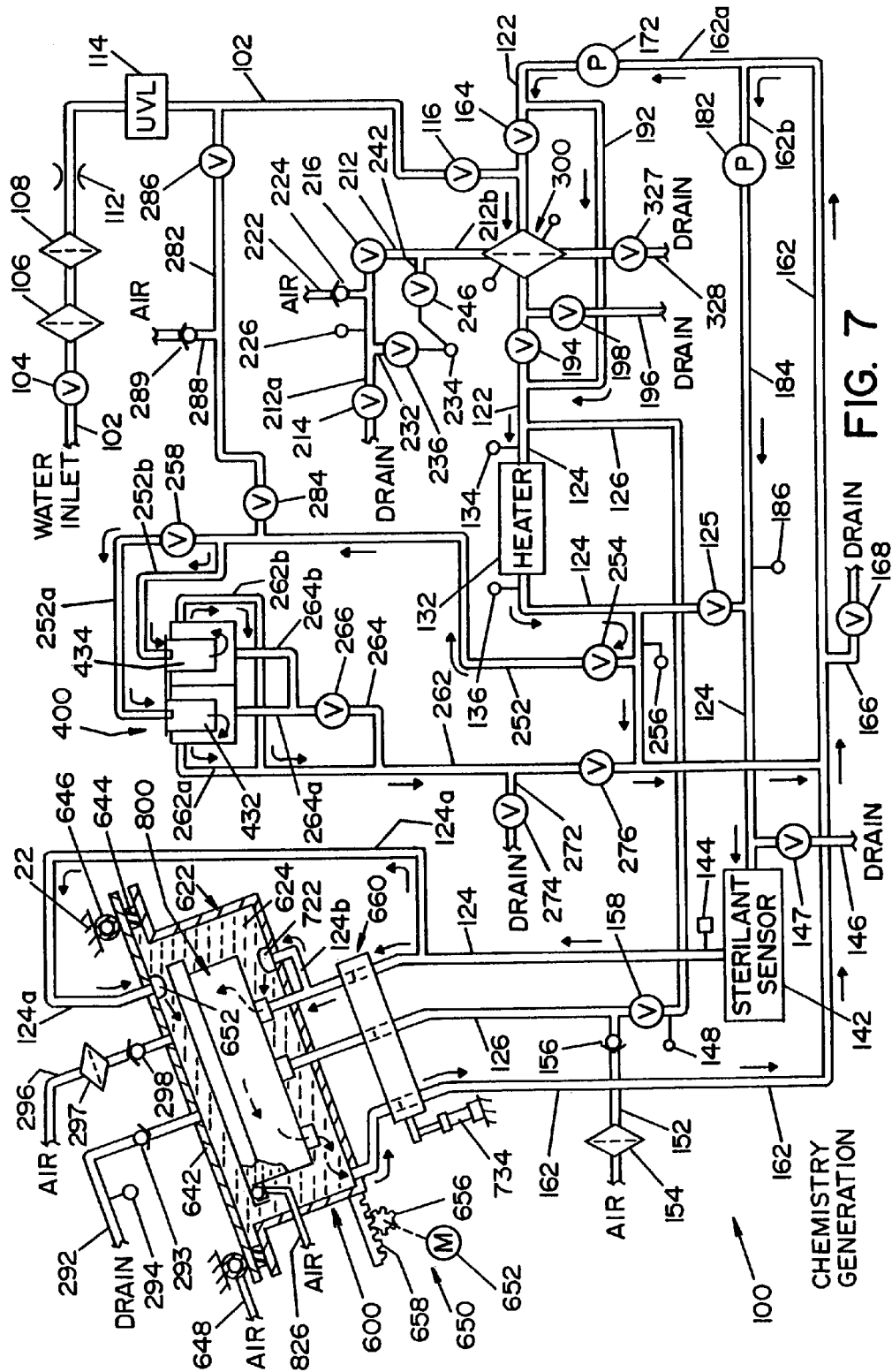
FIG. 7 is a schematic diagram of the reprocessor, illustrating the path of fluids through the reprocessor during a chemistry generation phase.

Once an alkaline fluid having a predetermined pH level is produced, valve 258 is opened to allow water to flow through container 432 in the chemistry-holding device 430. Because the apertures 576 are larger than apertures 578, the flow rate through apertures 576 will be 1 to 10% higher than the flow rate through apertures 578. Preferably, the flow rate through aperture 576 will be 3 to 7% higher than the flow rate through apertures 578. Ideally, the flow rate through aperture 576 will be 5% higher than the flow rate through aperture 578. In this respect, the flow rate through compartment 484 containing builder components will be lower than the flow rate through compartment 482 containing a chemical reagent. The ratio of flow rate through compartment 482 to the flow rate through compartment 484 is chosen to achieve optimal generation of a microbial deactivation fluid. In the embodiment heretofore described, container 432 preferably contains acetylsalicylic acid. When the dissolved builder components contact the acetylsalicylic acid, a microbial deactivation fluid is generated. As with container 434, water flowing through container 432 fills compartment 482 in housing 470 and exits chemistry-delivery system 400 through section 262*a* of chemistry-return line 262. In this respect, compartment 482 will be filled with fluid up to outlet line 262*a*. FIG. 7 generally illustrates the fluid flow through fluid-circulation system 100 during the chemistry-generation phase. As illustrated in FIG. 7, the microbial decontamination fluid will ultimately flow through sterilant sensor 142 that monitors the concentration thereof to ensure that a proper level of the decontaminating solution is within the fluid.

Exposure Phase

Figure 8:
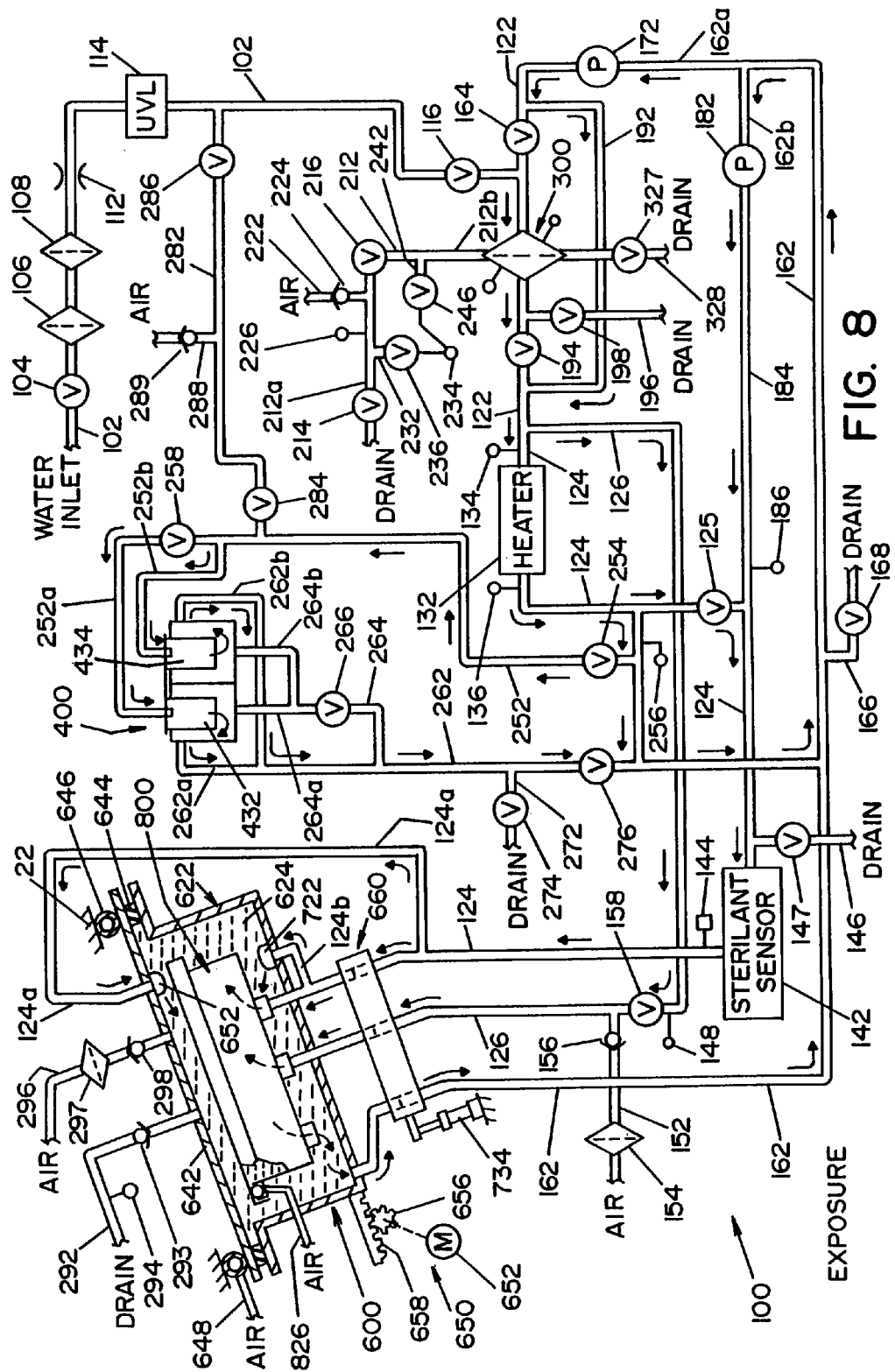
FIG. 8 is a schematic diagram of the reprocessor, illustrating the path of fluids through the reprocessor during an instrument exposure phase.

During the exposure phase, the microbial deactivation fluid formed in the chemistry-generation phase is conveyed throughout fluid-circulation system 100 as schematically illustrated in FIG. 8. The microbial deactivation fluid flowing through first- and second-branch feeder lines 124, 126 flow into the decontamination chamber and into instrument container 800 therein. The deactivation fluid flowing into instrument container 800 is sprayed through spray nozzles 852 around the exterior of the medical instruments within container 800. Fluid flowing through branch feeder line 124 flows into cavity 874 within tray 812 and through connectors 848 into the lumens and passages within medical instruments 842. In this respect, deactivation fluid circulates through the decontamination chamber formed by drawer tray 622 and plate 642 and flows out of the chamber to return line 162. Similarly, fluid flows out of instrument container 800 through a return conduit to return line 162. During the exposure period, pumps 172 and 182 continuously pump fluid throughout fluid-circulation system 100. Pump 172 is the high-pressure pump that provides sufficient pressure to force deactivation fluid through filter element 300, heater 132, second branch feeder line 126, and through chemistry-delivery system 400. In a preferred embodiment, pump 172 is capable of pumping fluid at about 3.5 gallons per minute at about 40 psig. At these levels, there is sufficient force to flow through the restrictive filter element 300, lumen passages within medical instruments 842, heater 132 and chemistry-delivery system 400. Pump 172 is capable of pumping about 25% of the total fluid flow in the system. Pump 182, i.e., the high-volume pump, provides a larger amount of fluid at lower pressure to the decontamination chamber and the interior of instrument container 800. Pump 182 is capable of pumping about 75% of the total fluid flow in the system. Higher pressure fluid flowing through second branch feeder line 126 provides a lower volume but a higher pressure fluid and is connected to lumen passages within medical instruments 842 within instrument container 800. During the exposure phase, deactivation fluid is circulated throughout fluid-circulation system 100 and through the deactivation chamber and instrument container 800 for a pre-determined period of time. It is sufficient to decontaminate items within the instrument container and to decontaminate the components and fluid conduits of fluid-circulation system 100.

Drain Phase

Figure 9A:
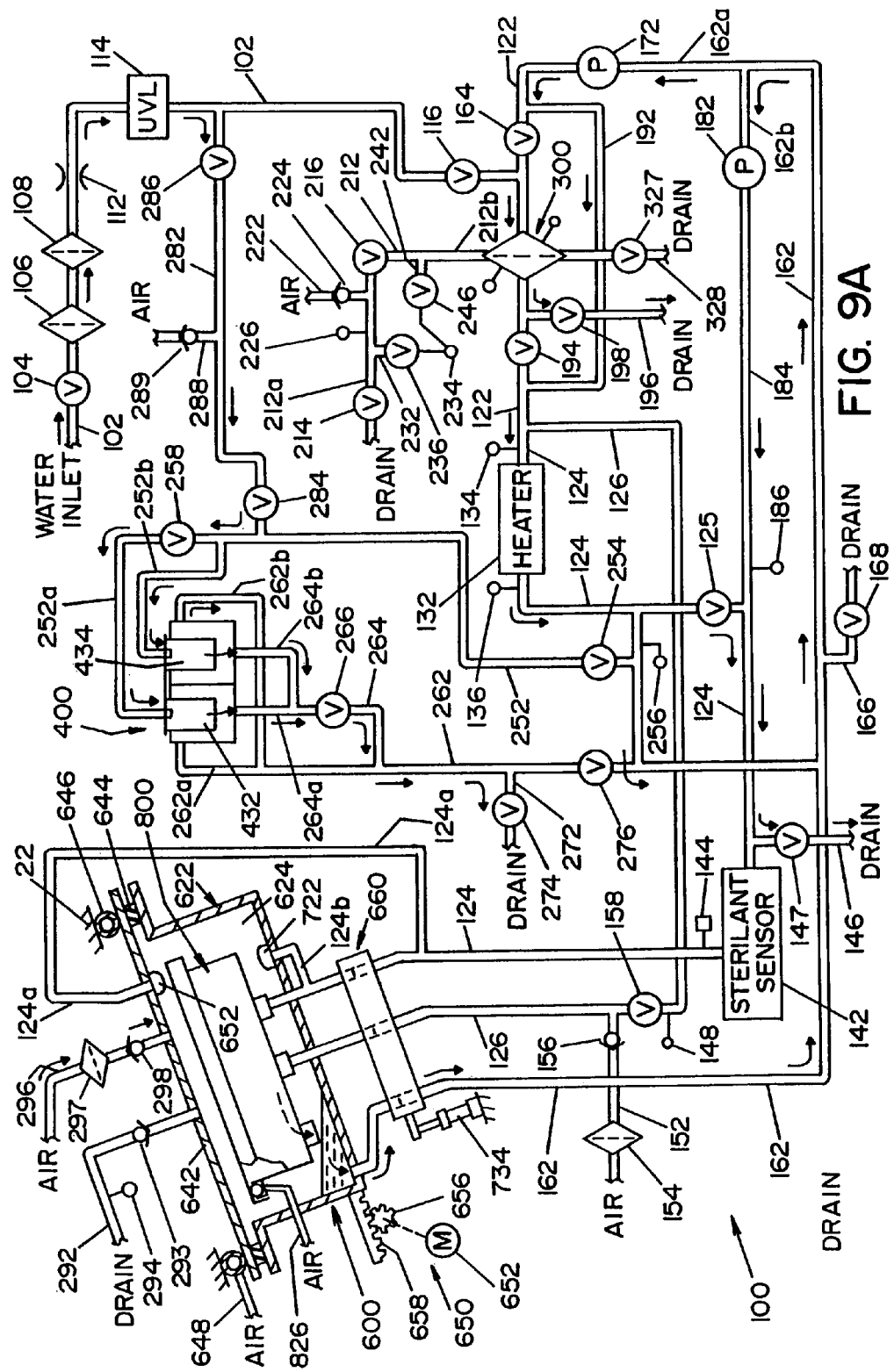
FIG. 9A is a schematic diagram of the reprocessor, illustrating the path of fluids through the reprocessor during a first part of a drain phase.
Figure 9B:
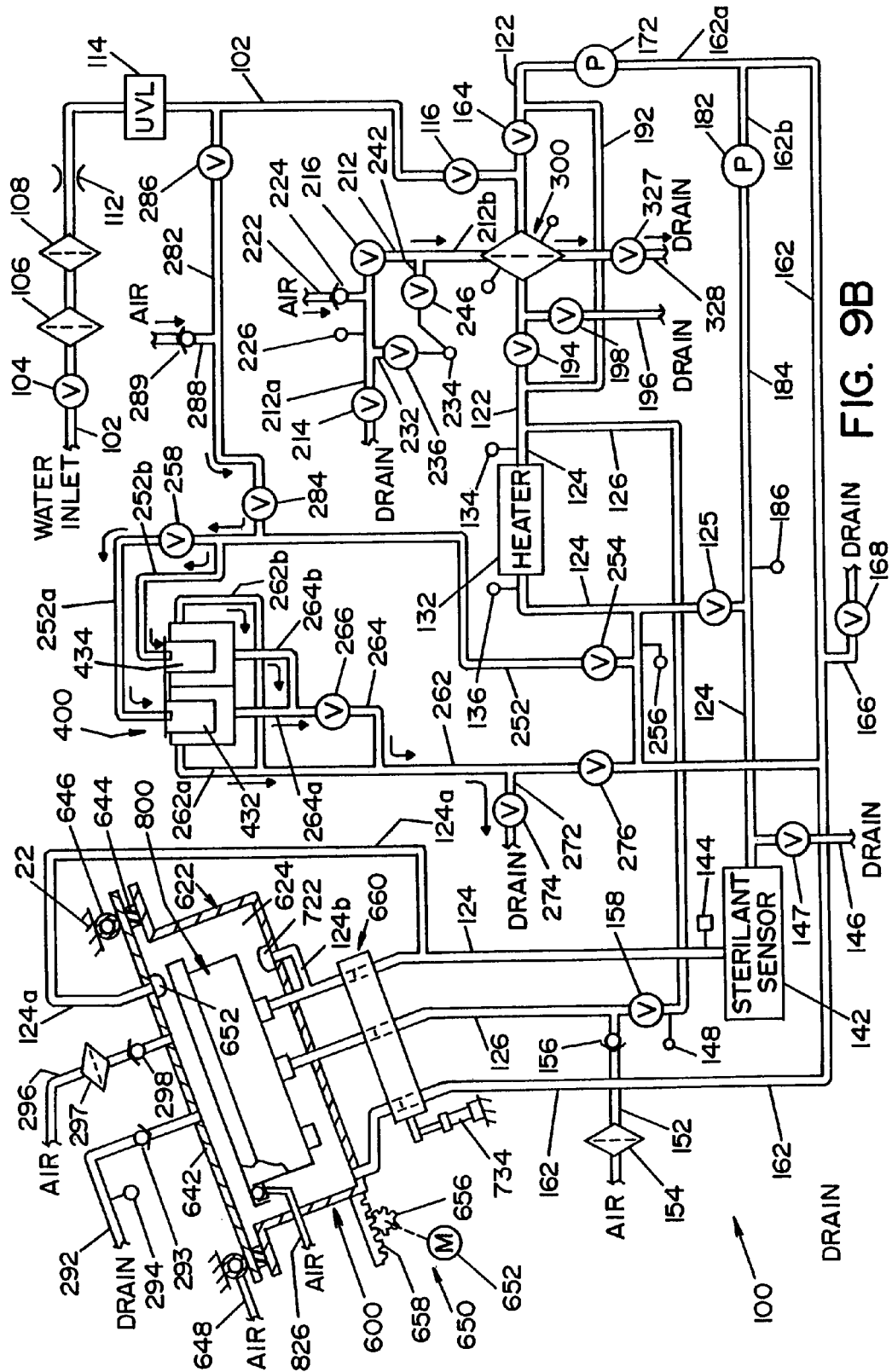
FIG. 9B is a schematic diagram of the reprocessor, illustrating the path of fluids through the reprocessor during a second part of the drain phase.

After a pre-determined exposure period, the system controller initiates a drain phase. The drain phase is comprised basically of two steps, best seen in FIGS. 9A and 9B. During the drain phase, valves 254 and 276 to the chemical-delivery system are closed to prevent flow thereto. Valves 147, 198, and 274 in drain lines 146, 196, and 272, respectively, are opened. Pumps 172, 182 continue to operate for a pre-determined period of time, forcing the deactivation fluid in the decontamination chamber and instrument container 800 out through drain lines 146, 196, as illustrated in FIG. 9A. At the same time, valves 284, 286, are opened to connect chemistry-inlet line 252 to water-inlet line 102. Valve 104 is then opened to allow water to enter the system and flush chemistry-delivery system 400 as schematically illustrated in FIG. 9A. Water entering chemistry-delivery system 400 is drained from chemistry-delivery system 400 through drain line 272. In this respect, during the drain phase, fluid entering chemistry-delivery system 400 is not allowed to enter any portion of fluid circulation system 100 that is downstream of valve 276 or upstream of valve 254. After a pre-determined period of time sufficient to allow flushing of chemistry-delivery system 400 and after a period sufficient to allow draining of most of the fluid from fluid circulation system 100 through pumps 172, 182, pumps 172 and 182 are deactivated. Valve 104 is closed to stop the flow of water to chemistry-delivery system 400. Valve 286 in connecting line 282 is then closed. Air line 288 is connected to a source of filtered, dry, pressurized air that enters the chemistry-delivery system 400 through connecting line 282 and chemistry-inlet line 252. The air essentially blows the remaining water within chemistry-delivery system 400 out through drain line 272 and further dries the interior portions of chemistry-delivery system and the lines connecting thereto. In this respect, during the drain phase, air entering chemistry-delivery system 400 is not allowed to enter any portion of fluid circulation system 100 that is downstream of valve 276 or upstream of valve 254. As illustrated in FIG. 9A, valve 266 in drain line 264 is opened to allow compartments 482, 484 within housing 470 of chemistry-delivery system 400 to drain from the bottom. Similarly, pressurized, dried air is applied to air line 152 and, thus, is conveyed through the lower portion of fluid-circulation system 100 to blow out remaining fluid within the internal passages of the medical devices in the device container.

Once the drain phase has been completed, an indication is provided on the display panel 28 of housing structure 22. If a valve element 894 was installed into each connector inserts 692C, 692B, 692C, then actuator 908, schematically illustrated as a pin in FIGS. 25 and 26, moves valve element 894 from an open position to a closed position. At that time, the air pressure to bladder 646 is removed and springs 647 bias plate 642 and static seal 644 away from the surface of drawer tray 622. Drawer assembly 600 may then be moved to an open position by pressing drawer-activation button 634. With drawer assembly 600 in an open position, instrument container 800 can be removed from drawer tray 622. If container 800 includes valve element 894, or in the alternative, a valve element 1240, barrier 898 or filter element 1280, respectively, will prevent microbial decontamination of the interior of instrument container 800.

Storage of Instrument Container(s) 800

In accordance with one aspect of the present invention, the deactivated instruments may remain within instrument container 800 and may be stored for a pre-determined period of time, with the instruments in instrument container 800 remaining in a microbially deactivated environment. In this respect, instrument container 800 would be inserted into a compartment 1014 of storage cabinet 1000. Instrument container 800 would be inserted into a compartment 1014, wherein connections on the bottom of instrument container 800 engage and mate with connector 1026A, 1026B, 1026C on shelf 1022 of storage cabinet 1000.

As illustrated in the drawings, a plurality of instrument containers 800 may be inserted into storage cabinet 1000, with each instrument container 800 being in communication with the warm, air-circulation system.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. In an apparatus for deactivating medical instruments and devices having a circulation system for circulating a fluid through a decontamination chamber for holding medical instruments and devices, a method of generating a microbial deactivation fluid and exposing said devices to said microbial deactivation fluid for an instrument exposure period of time comprising the steps of:

(a) providing a first compartment and a second compartment in said circulation system;

(b) providing a chemical reagent in said first compartment and a builder composition in said second compartment;

(c) causing a fluid to flow through said second compartment to begin dissolving said builder composition to create an alkaline fluid that is conveyed through said decontamination chamber;

(d) circulating said alkaline fluid through said second compartment and said decontamination chamber until said alkaline fluid has reached a predetermined pH level, then causing said alkaline fluid to flow through said first compartment to begin dissolving said chemical reagent to generate a microbial deactivation fluid;

(e) continuing steps (c) and (d) to continue the generation of said microbial deactivation fluid; and (f) maintaining the concentration of said microbial deactivation fluid flowing through said decontamination chamber at a predetermined concentration for an instrument exposure period of time by continuously flowing said fluid at a first flow rate through said first compartment and at a second flow rate through said second compartment during said instrument exposure period of time such that the ratio of said first flow rate to said second flow rate results in optimal generation of said microbial deactivation fluid during said instrument exposure period of time.

2. A method as defined in claim 1, further comprising the step of:
- (g) causing said microbial deactivation fluid to flow through said decontamination chamber at a predetermined temperature.

3. A method as defined in claim 2, wherein said predetermined temperature is between about 50° C. and about 60° C.

4. A method as defined in claim 1, wherein said predetermined pH level is between about 8.0 and about 9.0.

5. A method as defined in claim 1, wherein said predetermined minimum concentration of said microbial deactivation fluid is between about 1250 ppm and about 2000 ppm.

6. A method as defined in claim 1, wherein said chemical reagent is acetylsalicylic acid.

7. A method as defined in claim 1, wherein said builder composition includes a per-salt.

8. A method as defined in claim 7, wherein said per-salt is sodium perborate.

9. In an apparatus for deactivating medical instruments and devices having a circulation system for circulating a fluid through a decontamination chamber for holding medical instruments and devices, a method of generating a microbial deactivation fluid comprising the steps of:
- (a) providing a first compartment and a second compartment in said circulation system;
- (b) providing a chemical reagent in said first compartment and a builder composition in said second compartment;
- (c) causing said fluid having a temperature between about 45° C. and about 60° C. to flow through said second compartment to begin dissolving said builder composition to create an alkaline fluid in said decontamination chamber; and
- (d) when said alkaline fluid in said decontamination chamber has reached a predetermined pH level, causing said alkaline fluid to flow through said first compartment to begin dissolving said chemical reagent to generate a microbial deactivation;
- (e) maintaining the concentration of said microbial deactivation fluid flowing through said decontamination chamber at a predetermined concentration for an instrument exposure period of time by continuously dissolving said chemical reagent at a first rate and said builder composition at a second rate during said instrument exposure period of time.

10. A method as defined in claim 9, further comprising the step of:
- (f) causing said microbial deactivation fluid to flow through said decontamination chamber at a predetermined temperature.

11. A method as defined in claim 10, wherein said predetermined temperature is between about 50° C. and about 60° C.

12. A method as defined in claim 9, wherein said predetermined pH level is between about 8.0 and about 9.0.

13. A method as defined in claim 9, wherein said chemical reagent is acetylsalicylic acid.

14. A method as defined in claim 9, wherein said builder composition includes a per-salt.

15. A method as defined in claim 14, wherein said per-salt is sodium perborate.

16. In an apparatus for deactivating medical instruments and devices having a circulation system for circulating a fluid through a decontamination chamber for holding medical instruments and devices, a method of generating a microbial deactivation fluid comprising the steps of:
- (a) providing a first compartment and a second compartment in said circulation system;
- (b) providing a chemical reagent in said first compartment and a builder composition in said second compartment;
- (c) causing said fluid to flow through said second compartment to begin dissolving said builder composition to create an alkaline fluid in said decontamination chamber;
- (d) when said alkaline fluid in said decontamination chamber has reached a predetermined pH level, causing said alkaline fluid to flow through said first compartment to begin dissolving said chemical reagent to generate a microbial deactivation fluid; and
- (e) maintaining the concentration of said microbial deactivation fluid flowing through said decontamination chamber at a predetermined concentration for an instrument exposure period of time by continuously dissolving said chemical reagent at a first rate and said builder composition at a second rate during said instrument exposure period of time.

17. A method as defined in claim 16, wherein said predetermined pH level is between about 8.0 and about 9.0.

18. A method as defined in claim 16, wherein said chemical reagent is acetylsalicylic acid.

19. A method as defined in claim 16, wherein said builder composition includes a per-salt.

20. A method as defined in claim 19, wherein said per-salt is sodium perborate.

21. In an apparatus for deactivating medical instruments and devices having a circulation system for circulating a fluid through a decontamination chamber for holding medical instruments and devices, a method of generating a microbial deactivation fluid comprising the steps of:
- (a) providing a first compartment and a second compartment in said circulation system;
- (b) providing a chemical reagent in said first compartment and a builder composition in said second compartment;
- (c) causing said fluid to flow through said second compartment to begin dissolving said builder composition to create an alkaline fluid in said decontamination chamber;
- (d) after a predetermined amount of time, causing said alkaline solution to flow through said first compartment to begin dissolving said chemical reagent to generate a microbial deactivation fluid; and
- (e) maintaining the concentration of said microbial deactivation fluid flowing through said decontamination chamber at a predetermined concentration for an instrument exposure period of time by continuously dissolving said chemical reagent at a first rate and said builder composition at a second rate during said instrument exposure period of time.

22. A method as defined in claim 21, wherein said predetermined amount of time is based on said alkaline solution achieving a predetermined pH level.

23. A method as defined in claim 22, wherein said predetermined pH level is between about 8.0 and about 9.0.

24. A method as defined in claim 21, wherein said chemical reagent is acetylsalicylic acid.

25. A method as defined in claim 21, wherein said builder composition includes a per-salt.

26. A method as defined in claim 25, wherein said per-salt is sodium perborate.

27. A method as defined in claim 2, further comprising the steps of:
- h) fluidly isolating said first compartment and said second compartment from said circulation system;

i) conveying a rinse water through said first compartment and said second compartment to remove residual microbial deactivation fluid therefrom; and j) conveying a pressurized air through said first compartment and said second compartment to remove said rinse water therefrom.

28. A method as defined in claim 1, wherein said first flow rate is faster than said second flow rate.

29. A method as defined in claim 1, wherein said first flow rate causes said chemical reagent to dissolve at a first rate and said second flow rate causes said builder composition to dissolve at a second rate.

* * * * *